US012285597B2

United States Patent
Harjes et al.

(10) Patent No.: US 12,285,597 B2
(45) Date of Patent: Apr. 29, 2025

(54) CIRCULATORY SUPPORT SYSTEMS INCLUDING CONTROLLER AND PLURALITY OF SENSORS AND METHODS OF OPERATING SAME

(71) Applicant: TC1 LLC, St. Paul, MN (US)

(72) Inventors: Daniel I. Harjes, Carlisle, MA (US); Nichole Mercier, Pelham, NH (US)

(73) Assignee: TC1 LLC, St. Paul, MN (US)

( * ) Notice: Subject to any disclaimer, the term of this patent is extended or adjusted under 35 U.S.C. 154(b) by 1093 days.

(21) Appl. No.: 16/949,146

(22) Filed: Oct. 15, 2020

(65) Prior Publication Data

US 2021/0121617 A1    Apr. 29, 2021

Related U.S. Application Data

(60) Provisional application No. 62/926,141, filed on Oct. 25, 2019.

(51) Int. Cl.
*A61M 60/50* (2021.01)
*A61M 60/135* (2021.01)
*A61M 60/422* (2021.01)

(52) U.S. Cl.
CPC .......... *A61M 60/50* (2021.01); *A61M 60/135* (2021.01); *A61M 60/422* (2021.01);
(Continued)

(58) Field of Classification Search
CPC .. A61M 60/60; A61M 60/135; A61M 60/422; A61M 2205/3327; A61M 2205/3331; A61M 2230/04
See application file for complete search history.

(56) References Cited

U.S. PATENT DOCUMENTS 4,763,032 A    8/1988  Bramm et al.
5,921,913 A    7/1999  Siess
(Continued)

FOREIGN PATENT DOCUMENTS

JP    2005514973 A    5/2005
JP    2012115619 A    6/2012
(Continued)

OTHER PUBLICATIONS

International Search Report and Written Opinion for International Patent App. No. PCT/US2020/055716, mailed May 11, 2021, 23 pages.

*Primary Examiner* — James M Kish
*Assistant Examiner* — Roland Dinga
(74) *Attorney, Agent, or Firm* — Armstrong Teasdale LLP

(57) ABSTRACT

A circulatory support system includes an implantable blood pump including a housing, a rotor operable to pump blood from an inlet to an outlet, a stator, and at least two of the following: a current sensor, a rotor position sensor, an accelerometer, and a pressure sensor. The controller is connected to the sensors and includes a signal-processing module configured to receive, from each of the sensors, a data stream. The signal-processing module is also configured to filter the data streams received from the plurality of sensors, determine at least one of a pump operating parameter, a cardiac characteristic, and a pump control parameter based on at least two of the filtered data streams, and output the at least one of the pump operating parameter, the cardiac characteristic, and the pump control parameter to at least one of the operator interface module and the pump control module.

22 Claims, 11 Drawing Sheets

(52) U.S. Cl.
CPC ............... *A61M 2205/3327* (2013.01); *A61M 2205/3331* (2013.01); *A61M 2230/04* (2013.01)

(56) References Cited

U.S. PATENT DOCUMENTS

| | | |
|---|---|---|
| 8,177,838 B2 | 5/2012 | Vodermayer et al. |
| 9,849,224 B2 | 12/2017 | Angwin et al. |
| 2003/0199727 A1 | 10/2003 | Burke et al. |
| 2004/0152944 A1* | 8/2004 | Medvedev .......... A61M 60/546 600/17 |
| 2014/0200389 A1* | 7/2014 | Yanai .................. A61M 60/216 600/16 |
| 2014/0296615 A1 | 10/2014 | Franano |
| 2015/0290374 A1* | 10/2015 | Bourque ............. A61M 60/422 600/17 |
| 2015/0290375 A1* | 10/2015 | Angwin .............. A61M 60/216 600/16 |
| 2016/0166211 A1 | 6/2016 | Brown et al. |
| 2018/0280601 A1 | 10/2018 | Harjes et al. |
| 2018/0353667 A1 | 12/2018 | Moyer et al. |
| 2018/0361043 A1 | 12/2018 | Granegger |
| 2018/0361044 A1 | 12/2018 | Wiesener et al. |
| 2022/0233084 A1* | 7/2022 | Valdez ................. A61B 5/6882 |

FOREIGN PATENT DOCUMENTS

| | | |
|---|---|---|
| JP | 2020528307 A | 9/2020 |
| WO | 2019154764 A1 | 8/2019 |

* cited by examiner

CIRCULATORY SUPPORT SYSTEMS INCLUDING CONTROLLER AND PLURALITY OF SENSORS AND METHODS OF OPERATING SAME

CROSS-REFERENCE TO RELATED APPLICATIONS

This application claims priority to U.S. Provisional Patent Application Ser. No. 62/926,141 filed Oct. 25, 2019, the disclosure of which is hereby incorporated by reference in its entirety.

BACKGROUND OF THE DISCLOSURE a. Field of the Disclosure

The present disclosure relates generally to mechanical circulatory support systems, and more specifically relates to implantable blood pump assemblies that include a plurality of sensors and a controller that combines data streams received from the sensors.

b. Background

Ventricular assist devices, known as VADs, are implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

A controller can be used to control operation of the implanted VAD. The controller can be operatively connected to the VAD via a wired, wireless, and/or mechanical connection, which can be used to supply the VAD with operating power (e.g., electrical and/or mechanical power) and control signals to control the operation of the VAD.

At least some VADs utilize feedback from one or more sensors to control operation of the VAD. Some VADs, for example, use a pressure sensor to measure pressure and monitor a patient's cardiac cycle for control of the VAD. While the sensors of at least some VADs provide valuable information, there are drawbacks with the quality and scope of the information provided by the sensors. For example, sometimes sensors are unable to provide accurate information due to malfunction and/or limitations in operational capabilities of the sensors. For example, some sensors, such as current sensors, may not provide usable information during all stages of heart or pump cycles. Further, it may be difficult to determine if individual sensors are providing accurate information. In addition, certain values, such as cardiac characteristics or pump operating parameters, cannot be determined from data provided by individual sensors alone and, therefore, individual sensors may provide less than optimal clinical information for operating the VAD.

Accordingly, a need exists for improved VADs that combine information from multiple sensors to monitor a patient's cardiac cycle and/or control operation of the VAD.

SUMMARY OF THE DISCLOSURE

The present disclosure is directed to a circulatory support system including an implantable blood pump and a controller. The implantable blood pump includes a housing defining an inlet, an outlet, a flow path extending from the inlet to the outlet, and an internal compartment separated from the flow path. The implantable blood pump also includes a rotor positioned within the flow path and operable to pump blood from the inlet to the outlet, and a stator positioned within the internal compartment and operable to drive the rotor. The implantable blood pump further includes a plurality of sensors including at least two of the following: a current sensor configured to detect a current provided to the stator, a rotor position sensor configured to detect a position of the rotor relative to the housing, an accelerometer configured to detect acceleration of the blood pump in at least one direction, and a pressure sensor positioned between the inlet and the outlet and configured to detect a pressure of blood flowing through the flow path. The controller is connected to the plurality of sensors and includes a signal-processing module and at least one of an operator interface module and a pump control module. The signal-processing module is configured to receive, from each of the plurality of sensors, a data stream. The signal-processing module is also configured to filter the data streams received from the plurality of sensors, determine at least one of a pump operating parameter, a cardiac characteristic, and a pump control parameter based on at least two of the filtered data streams, and output the at least one of the pump operating parameter, the cardiac characteristic, and the pump control parameter to at least one of the operator interface module and the pump control module.

The present disclosure is also directed to a method of operating an implantable blood pump. The blood pump includes a housing defining an inlet, an outlet, a flow path extending from the inlet to the outlet, and an internal compartment separated from the flow path. The blood pump also includes a rotor positioned within the flow path and operable to pump blood from the inlet to the outlet, and a stator positioned within the internal compartment and operable to drive the rotor. The method includes detecting, using a plurality of sensors, at least two of the following: a current provided to the stator, a position of the rotor relative to the housing, an acceleration of the blood pump in at least one direction, and a pressure of blood flowing through the flow path. The method also includes receiving, at a signal-processing module of a controller connected to the plurality of sensors, a data stream from each of the plurality of sensors, and filtering, by the controller, the data streams received from the plurality of sensors. The method further includes determining, by the controller, at least one of a pump operating parameter, a cardiac characteristic, and a pump control parameter based on at least two of the filtered data streams, and outputting the at least one of the pump operating parameter, the cardiac characteristic, and the pump control parameter from the signal-processing module to at least one of an operator interface module and a pump control module.

The present disclosure is further directed to an implantable blood pump including a housing defining an inlet, an outlet, a flow path extending from the inlet to the outlet, and an internal compartment separated from the flow path. The implantable blood pump also includes a rotor positioned within the flow path and operable to pump blood from the inlet to the outlet, a stator positioned within the internal compartment and operable to drive the rotor, and a plurality of sensors. The plurality of sensors includes a current sensor configured to detect a current provided to the stator, a rotor position sensor configured to detect a position of the rotor relative to the housing, an accelerometer configured to detect acceleration of the blood pump in at least one direction, and a pressure sensor positioned between the inlet and the outlet and configured to detect a pressure of blood flowing through the flow path. The plurality of sensors are connected to a controller configured to receive a data stream from each of the plurality of sensors, filter the data streams received from the plurality of sensors, and determine at least one of a pump operating parameter, a cardiac characteristic, and a pump control parameter based on the filtered data streams.

DETAILED DESCRIPTION OF THE DISCLOSURE

The present disclosure is directed to implantable blood pump assemblies. Embodiments of the implantable blood pump assemblies disclosed herein include a plurality of sensors that are connected to a controller. For example, in some embodiments, the plurality of sensors include a current sensor, a rotor position sensor, an accelerometer, and a pressure sensor. A signal-processing module of the controller receives data streams from each of the plurality of sensors and filters the data streams. In some embodiments, at least one supplemental data stream is generated based on the data streams of the plurality of sensors. For example, the supplemental data stream may include a pressure of blood flowing out of the blood pump assembly through an outlet. Based on the filtered data streams, the controller may determine at least one of a pump operating parameter, a cardiac characteristic, and a pump control parameter. The pump operating parameter, cardiac characteristic, or pump control parameter may be output to an operator interface module for presentation to an operator and/or output to a pump control module configured to control the blood pump assembly.

Further, the data streams may be compared and combined to provide clinical and operational information that is more robust and accurate than information based on individual data streams alone. In some embodiments, the accuracy of each data stream may be determined based on a comparison of the data streams and each data stream may be assigned a quality rating based on the determined accuracy of the data streams. As a result, the implantable blood pump assemblies described herein may provide more accurate and more complete information for clinical assessment of a patient than prior blood pump assemblies. In addition, the implantable blood pump assemblies may be at least partially autonomously operated based on the multiple data streams.

Figure 1:
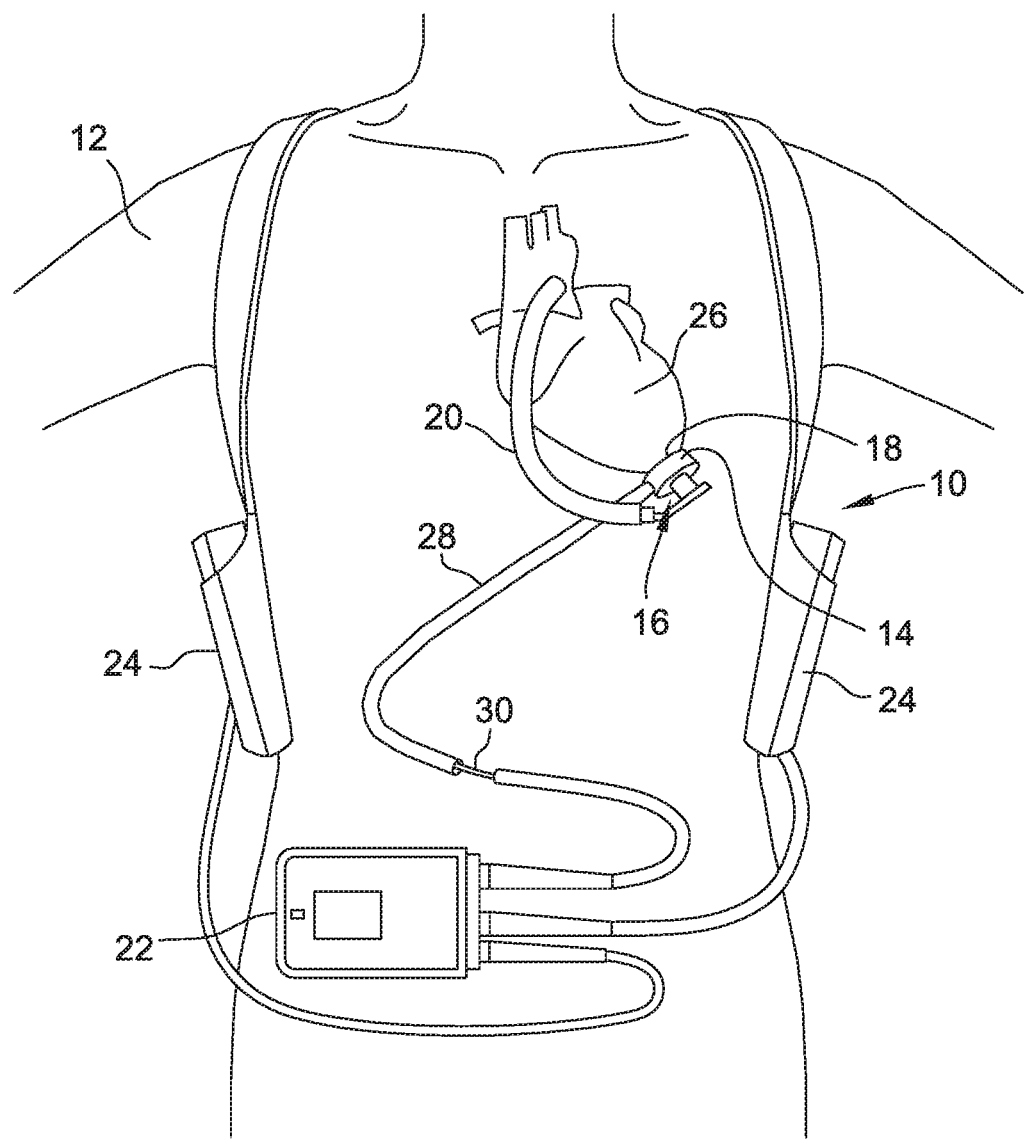
FIG. 1 is an illustration of a mechanical circulatory support system implanted in a patient's body.

Referring now to the drawings, FIG. 1 is an illustration of a mechanical circulatory support system 10 implanted in a patient's body 12. The mechanical circulatory support system 10 includes an implantable blood pump assembly 14 that includes a blood pump 16, a ventricular cuff 18, and an outflow cannula 20. The mechanical circulatory support system 10 also includes an external system controller 22 and one or more power sources 24 (e.g., batteries).

The blood pump assembly 14 can be implemented as or can include a ventricular assist device (VAD) that is attached to an apex of the left ventricle, as illustrated, or the right ventricle, or both ventricles of the heart 26. The blood pump assembly 14 can be attached to the heart 26 via the ventricular cuff 18 which is sewn to the heart 26 and coupled to the blood pump assembly 14. The other end of the blood pump assembly 14 connects to the ascending or descending aorta via the outflow cannula 20 so that the blood pump assembly 14 effectively diverts blood from the weakened ventricle and propels it to the aorta for circulation to the rest of the patient's vascular system. The VAD can include a centrifugal (as shown) or axial flow pump as described in further detail herein that is capable of pumping the entire output delivered to the left ventricle from the pulmonary circulation (i.e., up to 10 liters per minute).

FIG. 1 illustrates the mechanical circulatory support system 10 during battery powered operation. A communication line 28 connects the implanted blood pump assembly 14 to the external system controller 22, which monitors system 10 operation. In the illustrated embodiment, the communication line 28 is shown as a driveline that exits through the patient's abdomen 30, although it should be understood that the blood pump assembly 14 may be connected to the external system controller 22 via any suitable communication line, including wired and/or wireless communication. The system can be powered by either one, two, or more power sources 24. It will be appreciated that although the system controller 22 and power source 24 are illustrated outside/external to the patient body, the communication line 28, system controller 22 and/or power source 24 can be partially or fully implantable within the patient, as separate components or integrated with the blood pump assembly 14.

Figure 2:
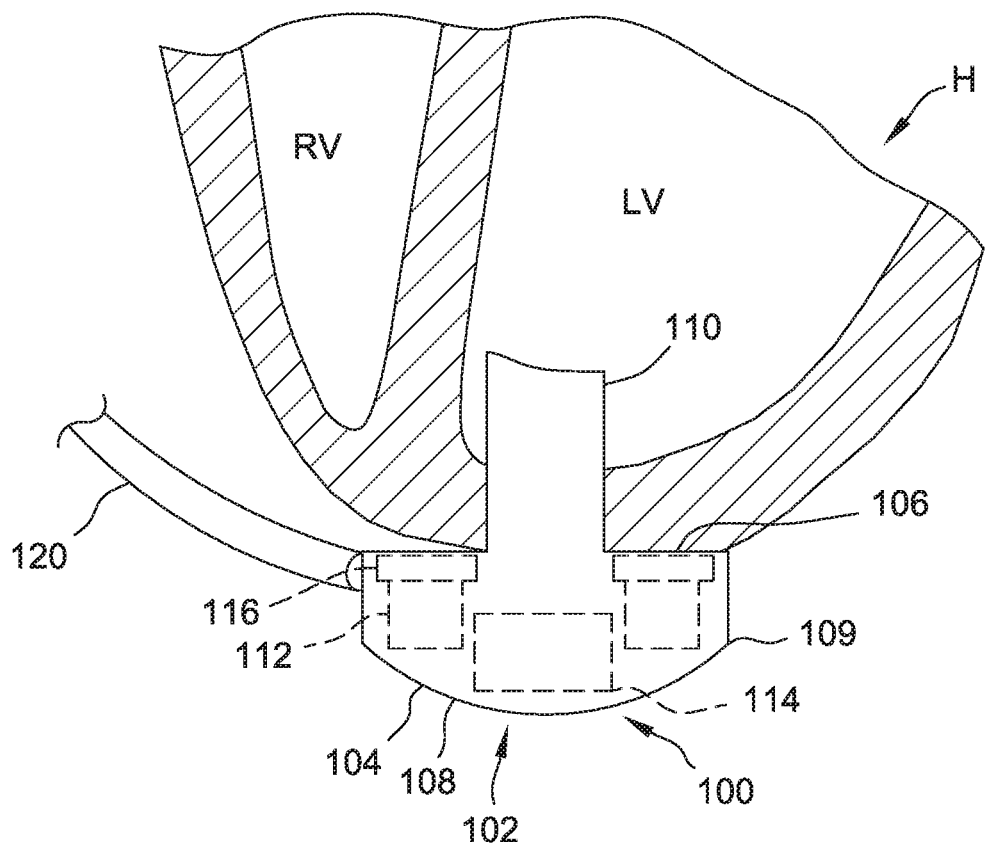
FIG. 2 is an illustration of a blood pump assembly suitable for use in the mechanical circulatory support system of FIG. 1, the blood pump assembly shown in an operational position implanted in a patient's body.

FIG. 2 is an illustration of an implantable blood pump assembly 100 suitable for use in the mechanical circulatory support system 10 of FIG. 1, where the blood pump assembly 100 is shown in an operational position implanted in a patient's body. In the illustrated embodiment, the blood pump assembly 100 is a left ventricular assist blood pump assembly connected to the left ventricle LV of the heart H.

The blood pump assembly 100 includes a blood pump 102 including a circular shaped housing 104 having a first outer face or wall 106 and a second outer face or wall 108. The blood pump assembly 100 further includes an inlet cannula 110 (generally, an inlet conduit) that, in the illustrated embodiment, extends from the first outer wall 106 of the pump housing 104. When the blood pump assembly 100 is implanted into a patient's body, as shown in FIG. 2, the first outer wall 106 of the housing 104 is positioned against the patient's heart H, and the second outer wall 108 of the housing 104 faces away from the heart H. The inlet cannula 110 extends into the left ventricle LV of the heart H to connect the blood pump assembly 100 to the heart H. The second outer wall 108 of the housing 104 has a chamfered edge 109 to avoid irritating other tissue that may come into contact with the blood pump assembly 100, such as the patient's diaphragm.

Figure 3:
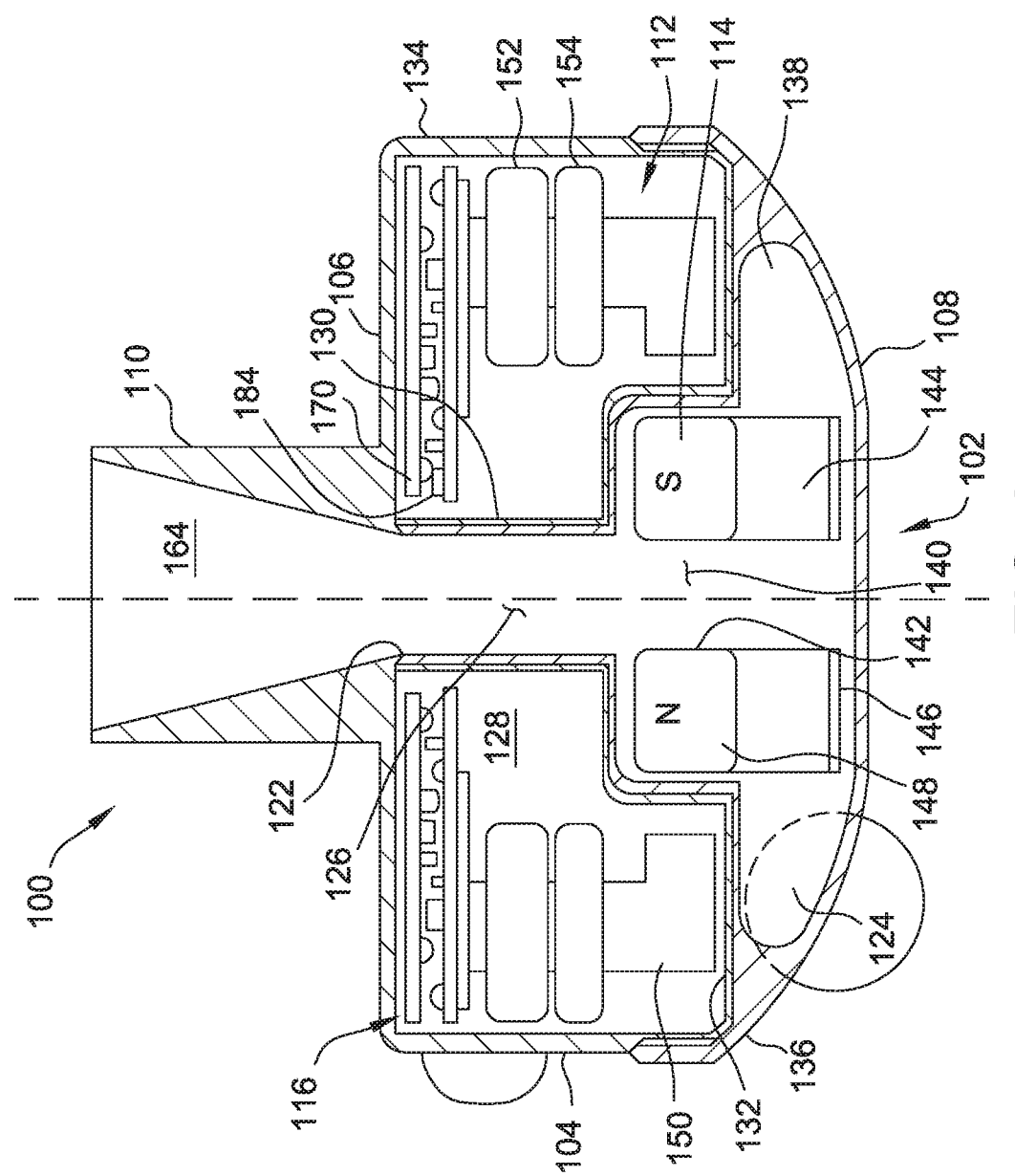
FIG. 3 is a schematic cross-sectional view of the blood pump assembly of FIG. 2.
Figure 4:
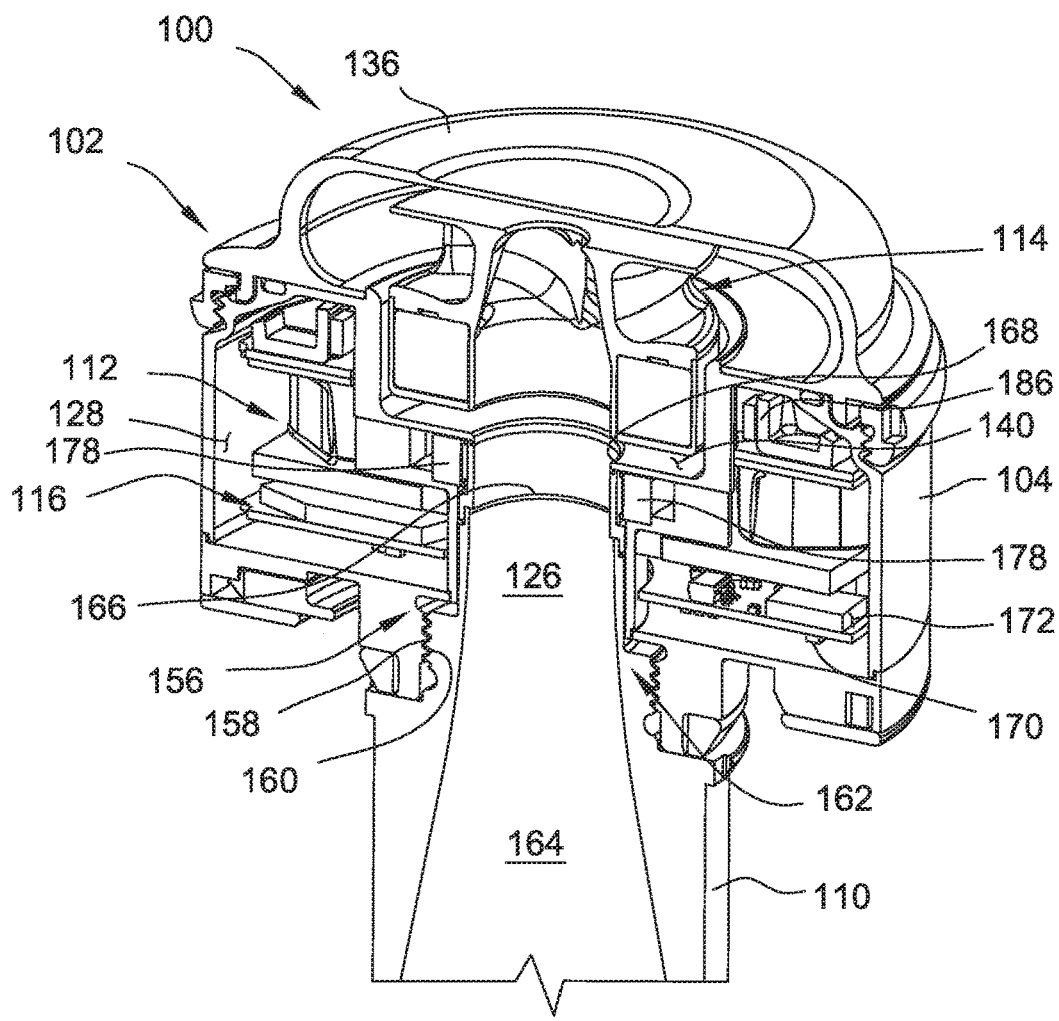
FIG. 4 is a perspective cut away view of the blood pump assembly of FIG. 2.
Figure 5:
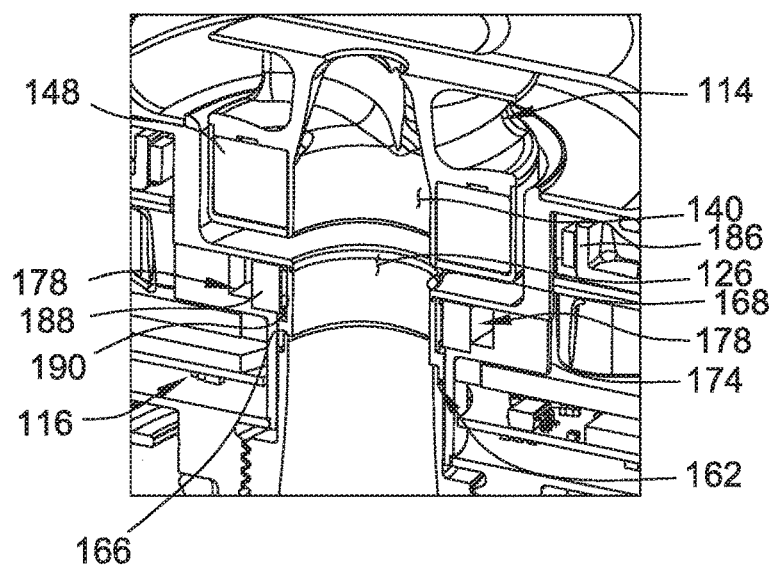
FIG. 5 is an enlarged view of the blood pump assembly of FIG. 4.

FIG. 3 is a schematic cross-sectional view of the blood pump assembly 100 of FIG. 2. FIG. 4 is a perspective cut away view of the blood pump assembly 100. FIG. 5 is an enlarged view of the blood pump assembly 100. The blood pump assembly 100 further includes a stator 112, a rotor 114, an on-board controller 116, and a plurality of sensors 118 (shown in FIG. 6). In the illustrated embodiment, the stator 112, the rotor 114, the on-board controller 116, and at least some of the plurality of sensors 118 are enclosed within the pump housing 104. In the illustrated embodiment, the stator 112 and the on-board controller 116 are positioned on the inflow side of the pump housing 104 toward the first outer wall 106, and the rotor 114 is positioned along the second outer wall 108. In other embodiments, the stator 112, the rotor 114, and the on-board controller 116 may be positioned at any suitable location within the pump housing 104 that enables the blood pump assembly 100 to function as described herein. Power is supplied to operational components of the blood pump assembly 100 (e.g., the stator 112 and the on-board controller 116) from a remote power supply via a power supply cable 120 (shown in FIG. 2).

The pump housing 104 defines an inlet 122 for receiving blood from a ventricle of a heart (e.g., left ventricle LV shown in FIG. 2), an outlet 124 for returning blood to a circulatory system, and a flow path 126 extending from the inlet 122 to the outlet 124. The pump housing 104 further defines an internal compartment 128 separated from the flow path 126, for example, by one or more dividing walls 130.

The pump housing 104 also includes an intermediate wall 132 located between the first outer wall 106 and the second outer wall 108, and a peripheral wall 134 that extends between the first outer wall 106 and the intermediate wall 132. Together, the first outer wall 106, the dividing wall 130, the intermediate wall 132, and the peripheral wall 134 define the internal compartment 128 in which the stator 112 and the on-board controller 116 are enclosed.

In the illustrated embodiment, the pump housing 104 also includes a cap 136 removably attached to the pump housing 104 along the intermediate wall 132. The cap 136 is threadably connected to the pump housing 104 in the illustrated embodiment, although in other embodiments the cap 136 may be connected to the pump housing 104 using any suitable connection means that enables the blood pump assembly 100 to function as described herein. In some embodiments, for example, the cap 136 is non-removably connected to the pump housing 104, for example, by welding. The removable cap 136 includes the second outer wall 108, the chamfered edge 109, and defines the outlet 124. The cap 136 also defines a volute 138 that is in fluid communication with the outlet 124, and a rotor chamber 140 in which the rotor 114 is positioned. The cap 136 can be attached to the pump housing 104 using any suitable connection structure. For example, the cap 136 can be engaged via threads with the peripheral wall 134 to seal the cap 136 in engagement with the peripheral wall 134.

The rotor 114 is positioned within the blood flow path 126, specifically, within the rotor chamber 140, and is operable to rotate in response to an electromagnetic field generated by the stator 112 to pump blood from the inlet 122 to the outlet 124. The rotor defines a central aperture 142 through which blood flows during operation of the blood pump 102. The rotor 114 includes impeller blades 144 located within the volute 138 of the blood flow path 126, and a shroud 146 that covers the ends of the impeller blades 144 facing the second outer wall 108 to assist in directing blood flow into the volute 138.

In the illustrated embodiment, the rotor 114 includes a permanent magnet 148 that defines the central aperture 142. The permanent magnet 148 has a permanent magnetic north pole N and a permanent magnetic south pole S for combined active and passive magnetic levitation of the rotor 114 and for rotation of the rotor 114. In operation, the stator 112 is controlled to drive (i.e., rotate) the rotor and to radially levitate the rotor 114 by generating electromagnetic fields that interact with the permanent magnetic poles S and N of the permanent magnet 148.

Any suitable stator 112 can be employed to rotate the rotor 114. The stator 112 generally includes a plurality of winding structures that generate suitable electromagnetic fields that interact with the rotor 114 to cause rotor 114 to rotate and levitate. In the illustrated embodiment, the stator 112 includes a plurality of pole pieces 150 arranged circumferentially at intervals around the dividing wall 130. The example blood pump assembly 100 includes six pole pieces 150, two of which are visible in FIG. 3. In other embodiments, the blood pump assembly 100 can include more than or less than six pole pieces, such as four pole pieces, eight pole pieces, or any other suitable number of pole pieces that enables the blood pump assembly 100 to function as described herein. In the illustrated embodiment, each of the pole pieces 150 includes a drive coil 152 for generating an electromagnetic field to rotate the rotor 114, and a levitation coil 154 for generating an electromagnetic field to control the radial position of the rotor 114.

Each of the drive coils 152 and the levitation coils 154 includes multiple windings of a conductor wound around the pole pieces 150. The drive coils 152 and the levitation coils 154 of the stator 112 are arranged in opposing pairs and are controlled to drive the rotor and to radially levitate the rotor 114 by generating electromagnetic fields that interact with the permanent magnetic poles S and N of the permanent magnet 148. Suitable methods for generating electromagnetic fields to rotate and radially levitate the rotor 114 are described, for example, in U.S. Pat. No. 9,849,224, the entire contents of which are incorporated herein by reference for all purposes. Although the drive coil 152 and levitation coil 154 are shown as separate coils in the illustrated embodiment, it should be understood that the drive coil 152 and levitation coil 154 may be implemented as a single coil configured to generate electromagnetic fields for both rotating and radially levitating the rotor 114.

The inlet cannula 110 is attached to the pump housing 104 at the inlet 122. As shown in FIG. 4, the pump housing 104 includes an inlet cannula receiving portion 156 that includes suitable connecting structure for connecting the inlet cannula 110 to the pump housing 104. In the illustrated embodiment, the pump housing 104 includes an internally threaded sleeve 158 that threadably engages external threads 160 on a downstream end 162 of the inlet cannula 110 to connect the inlet cannula 110 to the pump housing 104.

The inlet cannula 110 defines an inlet flow path 164 that supplies blood to the inlet 122 of the pump housing 104. As shown in FIG. 4, in the illustrated embodiment, the inlet cannula 110 extends into the blood flow path 126 defined by the pump housing 104 such that the inlet flow path 164 partially overlaps with the blood flow path 126.

The downstream end 162 of the inlet cannula 110 has a reduced cross-sectional area (e.g., relative to an upstream end of the inlet cannula 110) that produces a localized region of high velocity blood flow through the inlet flow path 164 and the blood flow path 126. Specifically, the cross-sectional area of the inlet flow path 164 gradually and continuously decreases towards the downstream end 162 of the inlet cannula 110 such that blood flowing through the inlet cannula 110 at a constant flow rate will experience an increase in velocity as it flows through the downstream end 162 of the inlet cannula 110. Consequently, during operation of the blood pump assembly 100, the reduced-cross-sectional area of the downstream end 162 produces a localized region of high velocity blood flow that flows through the inlet 122 and through the blood flow path 126.

In some embodiments, a portion 172 of the internal compartment 128 (shown in FIG. 4) is hermetically sealed from the portions of the internal compartment which may be in communication with fluid (e.g., blood) to inhibit fluid ingress into the portion of the internal compartment 128 in which electronics (e.g., stator 112 and on-board controller 116) are housed. In the illustrated embodiment, for example, a sensor assembly housing 174 forms a seal against the pump housing 104 to hermetically seal the portion 172 of the internal compartment 128 (shown in FIG. 4) in which electronics are housed from the internal cavity defined by the sensor assembly housing 174.

Figure 6:
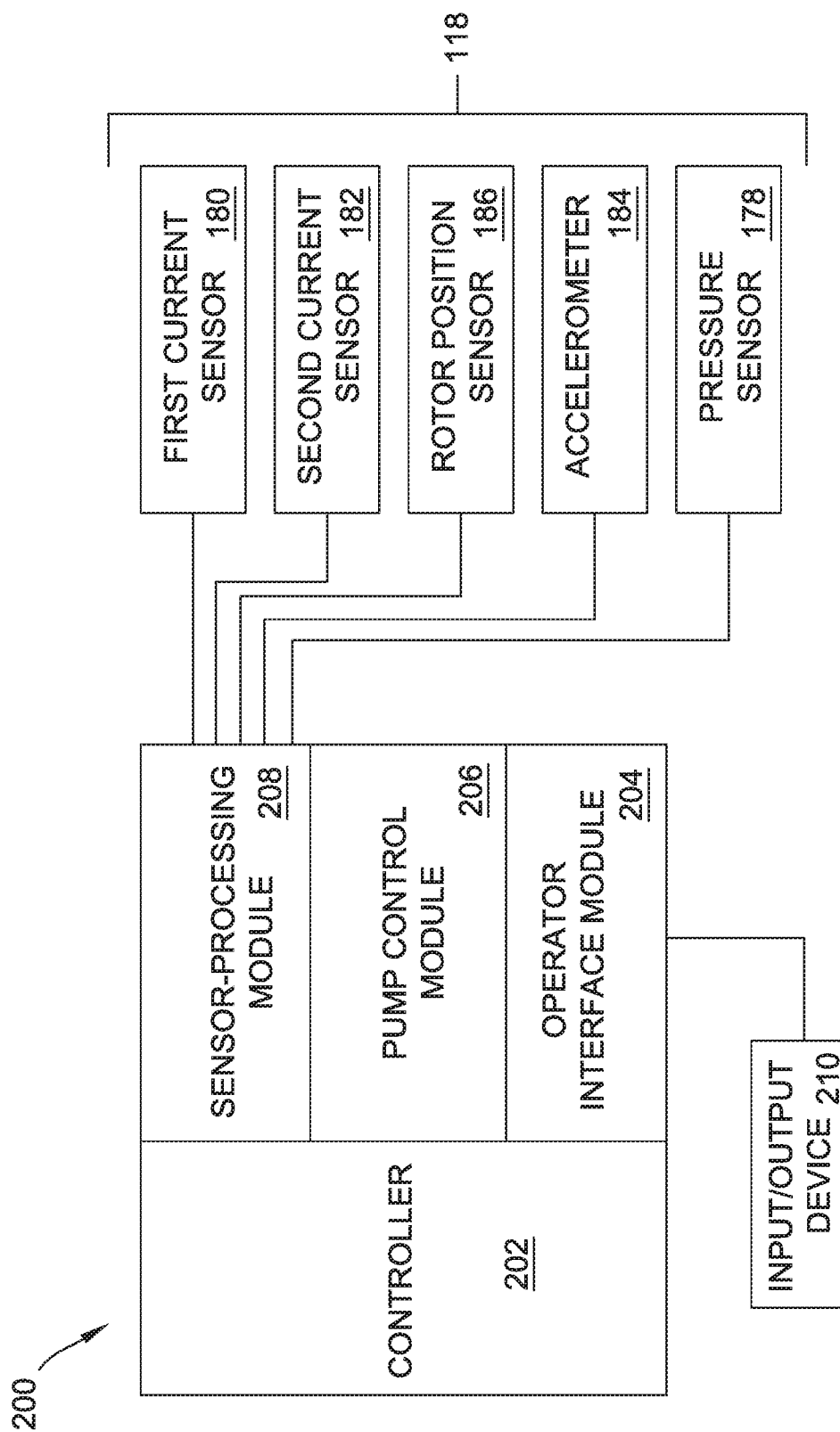
FIG. 6 is a schematic view of a portion of the blood pump assembly of FIGS. 2-5, the blood pump assembly including a controller connected to a plurality of sensors.

With additional reference to FIG. 6, the plurality of sensors 118 includes at least one pressure sensor 178, a first current sensor 180, a second current sensor 182, an accelerometer 184, and a rotor position sensor 186. The first current sensor 180 and the second current sensor 182 are configured to detect current provided to the stator 112. For example, the first sensor 180 is connected to the drive coils 152 and is configured to measure a current provided to the drive coils 152 of the stator 112 from the power supply. The second current sensor 182 is connected to the levitation coils 154 and is configured to measure a current provided to the levitation coils 154 of the stator 112 from the power supply. In other embodiments, the blood pump assembly 100 may include any suitable current sensors that enable the blood pump assembly 100 to operate as described herein. For example, in some embodiments, the blood pump assembly 100 includes a single current sensor that is configured to measure both the current provided to the drive coils 152 and the current provided to the levitation coils 154. In some embodiments, the first current sensor 180 and/or the second current sensor 182 are located outside of the housing 104. For example, in some embodiments, the first current sensor 180 and/or the second current sensor 182 may be connected to the controller 22 (shown in FIG. 1) and/or the power source 24 (shown in FIG. 1).

The rotor position sensor 186 is configured to detect a position of the rotor 114 relative to the stator 112. For example, in the illustrated embodiment, the rotor position sensor 186 is a Hall effect sensor which provides an output voltage that is directly proportional to the strength of a magnetic field that is located between the pole pieces 150 and the permanent magnet 148. The rotor position sensor 186 may provide the output voltage to the on-board controller 116 as a continuous data stream. The on-board controller 116 may continuously track the position of the rotor 114 by relating the data stream to a position of the rotor 114 relative to the stator 112. The data stream from the rotor position sensor 186 may be used to selectively attract and repel the permanent magnetic poles S and N of the permanent magnet 148 to adjust the position of the rotor 114 and/or cause the rotor 114 to rotate within the stator 112 during operation of the blood pump assembly 100.

In the illustrated embodiment, the blood pump assembly 100 includes two pressure sensors 178 configured to detect a pressure of blood flowing through the blood flow path 126. For example, as shown in FIGS. 5 and 6, in the illustrated embodiment, each pressure sensor 178 includes a sensing element 188 and a deflectable membrane 190 positioned between the sensing element 188 and the blood flow path 126. The blood pump assembly 100 can include more than or less than two pressure sensors 178 in other embodiments.

The pressure sensors 178 are located such that each of the pressure sensors 178 can detect the pressure of fluid flow through the blood flow path 126. For example, in the illustrated embodiment, the pressure sensors 178 are located adjacent the downstream end 162 of the inlet cannula 110, at the interface between the inlet cannula 110 and the pump housing 104. More specifically, the pressure sensors 178 are located between an outlet 166 of the inlet cannula 110 and an inlet 168 to the rotor chamber 140.

The accelerometer 184 of the example embodiment is mounted to a circuit board 170 of the on-board controller 116, and is configured to detect acceleration of the blood pump assembly 100 in at least one direction. For example, the accelerometer 184 may be a three-axis linear accelerometer configured to measure acceleration in three directions.

In the illustrated embodiment, the blood pump assembly 100 has an axis 192 about which the rotor 114 rotates. In the illustrated embodiment, the blood flow path 126 extends along the axis 192. The accelerometer is configured to detect acceleration of the blood pump assembly 100 in a first direction parallel to the axis 192, a second direction perpendicular to the axis 192, and a third direction perpendicular to the axis 192 and perpendicular to the second direction. The accelerometer is configured to provide a data stream to the controller 116 indicating the detected acceleration. In some embodiments, the on-board controller 116 is configured to determine a patient's activity level, the orientation of the blood pump 102, and/or a displacement of the blood pump 102 or heart wall based on acceleration in at least one of the first direction, the second direction, and the third direction. In other embodiments, the blood pump assembly 100 may include a plurality of accelerometers 184 and each accelerometer 184 may provide information on acceleration in at least one direction.

The on-board controller 116 can include one or more modules or devices that are enclosed within the pump housing 104. The on-board controller 116 can generally include any suitable computer and/or other processing unit, including any suitable combination of computers, processing units and/or the like that may be communicatively coupled to one another (e.g., on-board controller 116 can form all or part of a controller network). Thus, on-board controller 116 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit (ASIC), a digital signal processor (DSP), a field programmable gate array (FPGA), and other programmable circuits. Additionally, the memory device(s) of on-board controller 116 may generally include memory element(s) including, but not limited to, non-transitory computer readable medium (e.g., random access memory (RAM), read only memory (ROM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the on-board controller 116 to perform various functions including, but not limited to, controlling the supply of electrical current to the stator 112, determining a waveform relating to a pump operating parameter, a cardiac characteristic, or a pump control parameter, determining or calculating cardiac events or characteristics based on information provided by the plurality of sensors 118, such as heart rate, contractility, end-systolic pressure, end-diastolic pressure, atrial kick pressure, left ventricular contractility, max left ventricular pressure, and left ventricular relaxation, adjusting the speed of the rotor 114 based on information provided by the plurality of sensors 118 and/or one or more of the determined cardiac events or characteristics, outputting measurement data to an external controller (e.g., external system controller 22), and various other suitable computer-implemented functions. In addition, the memory can be used to store patient specific parameters that are used by the on-board controller 116 to control patient specific operational aspects of the blood pump assembly 100, as well as related software modules.

In the illustrated embodiment, the on-board controller 116 is implemented as one or more circuit boards 170 (shown in FIG. 4) and various components carried on the circuit boards (e.g., processors and memory devices) to control operation of the blood pump 102 by controlling the electrical supply to the stator 112.

A communication line (e.g., communication line 28 shown in FIG. 1) couples the blood pump assembly 100 and on-board controller 116 to the external system controller 22 (shown in FIG. 1), which monitors system operation via various software applications. As noted above, the blood pump assembly 100 itself also includes several software applications that are executable by the on-board controller 116 for various functions, such as to control radial levitation and/or drive of the rotor 114 of the pump assembly 100 during operation. The external system controller 22 can in turn be coupled to batteries 24 or a power module (not shown) that connects to an AC electrical outlet. The external system controller 22 can also include an emergency backup battery (EBB) to power the system (e.g., when the batteries 24 are depleted) and a membrane overlay, including Bluetooth capabilities for wireless data communication. An external computer that is configurable by an operator, such as clinician or patient, can further be coupled to the circulatory support system 10 for configuring the external system controller 22, the implanted blood pump assembly 100, and/or patient specific parameters, updating software on the external system controller 22 and/or the implanted blood pump assembly 100, monitoring system operation, and/or as a conduit for system inputs or outputs.

FIG. 6 is a schematic view of a sensing and control system 200 suitable for use in the mechanical circulatory support system 10 of FIG. 1. The sensing and control system 200 includes a controller 202 which, in some embodiments, may comprise at least one of controller 22 (shown in FIG. 1) and/or on-board controller 116 (shown in FIG. 3). The controller 202 includes an operator interface module 204, a pump control module 206, and a sensor-processing module 208. In some embodiments, one or more of the operator interface module 204, the pump control module 206, and the sensor-processing module 208 are located at a computing unit that is separate from the controller 22 and on-board controller 116.

Sensing and control system 200 further includes the plurality of sensors 118, which includes the pressure sensor 178, the first current sensor 180, the second current sensor 182, the accelerometer 184, and the rotor position sensor 186. The plurality of sensors 118 are connected to the controller 202 by suitable electrical conduits for receiving electrical power therefrom and sending signals thereto. For example, the signal-processing module 208 of the controller 202 is configured to receive a data stream from the pressure sensors 178, the first current sensor 180, the second current sensor 182, the accelerometer 184, and the rotor position sensor 186. In addition, the controller 202 may generate a supplemental data stream based on the data streams received from the plurality of sensors 118. For example, the controller 202 may determine a supplemental data stream indicating a pressure of the blood flowing out of the blood pump 102 through the outlet 124 based on measurements from the first current sensor 180 and at least one of the pressure sensors 178.

The signal-processing module 208 is configured to filter the data streams received from the plurality of sensors 118. For example, some of the data streams may include a waveform signal and the signal-processing module 208 may perform a waveform feature extraction on the data streams. During the waveform feature extraction process, the signal-processing module 208 identifies characteristics of the waveform signal that represent measured values such as bearing current, rotor position, blood flow through the blood pump assembly 100, pressure of the blood exiting the blood pump assembly 100 (e.g., aortic pressure), and pressure of blood entering the blood pump assembly 100 (e.g., left ventricle LV pressure). In addition, the signal-processing module 208 may identify patient activity level, pump orientation, and motion of the left ventricle LV based on the data streams from the accelerometer and/or other sensors of the plurality of sensors 118.

In some embodiments, the signal-processing module 208 may perform a spectral analysis on the data streams based on frequency spectrums. For example, in some embodiments, the spectral analysis includes applying a fast Fourier transform (FFT) to the data streams to identify characteristics of the data streams such as the frequency and amplitude content of any periodic signals in the data streams. In some embodiments, an FFT may be applied to the accelerometer data stream and the transformed data stream may indicate frequencies associated with a rotor spin rate (rotor speed and its harmonics) along with other vibratory signals such as vibrations from valve closing. The vibratory signals provide "heart sounds" (colloquially referred to as "lub dub" sounds) which can be interpreted in accordance with known diagnostic practices. For example, changes in amplitude of the heart sound frequencies may be used to detect a degree of valve opening and even to diagnose valvular disorders such as aortic regurgitation or stenosis.

Also, the signal-processing module 208 may be configured to remove noise or artifacts from the signal and/or adjust parameters of the waveform based on preset thresholds and ranges. In other words, the signal-processing module 208 "cleans-up" the raw data stream to provide a filtered data stream that is simpler for controller 202 to use in calculations and/or to output.

The controller 202 is also configured to compare the data streams and/or values determined based on the data streams, and determine a signal quality parameter for each data stream received at the signal-processing module from the sensors 118. For example, the controller 202 may determine a pump operating parameter, a cardiac characteristic, or a pump control parameter based on each data stream, and compare the determined values to each other to determine signal accuracy and reliability. In some embodiments, the controller 202 determines a value that is independently derivable from each data stream such as a heart rate. Based on the comparison, the controller 202 may associate a quality rating with each data stream or sensor 118. For example, if one of the determined values differs from at least one other determined value, the controller 202 may identify which of the values is more likely to be correct and associate a higher quality rating with the data stream that was used to determine the value. The controller 202 may associate a lower quality rating with the other data stream. In some embodiments, data streams with lower quality ratings (e.g., quality ratings below a preset threshold) are omitted from further computations.

In addition, the controller 202 can be configured to determine at least one of a pump operating parameter, a cardiac characteristic, and a pump control parameter based on the filtered data streams. For example, the controller 202 may determine any of the following based on the filtered data streams: heart rate, cycle timing, bearing current amplitude, displacement amplitude of rotor 114, maximum flow through the blood pump assembly 100, minimum flow through the blood pump assembly 100, average flow through the blood pump assembly 100, amplitude of the flow through the blood pump assembly 100, maximum rate of change of flow through the blood pump assembly 100, minimum rate of change of flow through the blood pump assembly 100, maximum aortic pressure, minimum aortic pressure, average aortic pressure, maximum rate of change of aortic pressure, minimum rate of change of aortic pressure, maximum left ventricle pressure, minimum left ventricle pressure, average left ventricle pressure, maximum rate of change of left ventricle pressure, minimum rate of change of left ventricle pressure, maximum left ventricle acceleration, pitch angle of blood pump assembly 100, yaw angle of the blood pump assembly 100, activity level of the patient, and degree of aortic valve opening.

For example, the controller 202 may be programmed to determine the heart rate of a patient by applying a fast Fourier transform to the pressure data collected by the pressure sensors 178, and/or by calculating a time interval between cardiac cycle detection points evident from the pressure waveform (e.g., beginning of systole, end of systole, beginning of diastole, and/or end of diastole). The controller 202 may also be programmed to determine ventricular filling pressure or minimum pressure, maximum pressure or maximum systolic pressure, pressure amplitude (i.e., the difference between maximum pressure and minimum pressure), average pressure, contractility (i.e., maximum systolic dP/dt), relaxation (i.e., minimum systolic dP/dt), end systolic pressure, end diastolic pressure, atrial kick pressure, and any other cardiac characteristic by applying mathematical operations to the data collected by the sensors 118.

Moreover, the controller 202 may combine two or more of the data streams to determine the pump operating parameter, the cardiac characteristic, and/or the pump control parameter. In some embodiments, the controller 202 combines data streams and provides a statistically weighted value. In other words, the controller 202 determines a statistical weight of each data stream based on the quality rating, preset criteria, and/or any other suitable factor, and calculates the value with the determined weights applied to each of the data streams.

For example, in some embodiments, the controller 202 may determine a heart rate value based on the accelerometer data stream, flow waveform data stream, and LV pressure waveform data stream by applying a fast Fourier transform to each data stream. Applying the FFT to the data streams may highlight peaks in the low frequency domain (e.g., the low frequency domain may be in a range of about 0.5 Hz to about 3.0 Hz) in each data stream, and a heart rate value may be determined based on each data stream. In some embodiments, the heart rate value determined based on the flow waveform data stream may be used as the derived value because the flow waveform data stream may have the highest quality and accuracy rating of the received data streams. For example, the flow waveform data stream may have a higher signal-to-noise and sampling rate than the accelerometer and LV pressure waveform data streams. However, the derived value may be compared to the heart rate values determined based on the accelerometer and LV pressure waveform data streams to provide a confidence rating for the derived value. For example, the derived value may have a high or strong confidence rating if one or both of the accelerometer and LV pressure waveform data streams provide a heart rate value that matches or is within a predetermined tolerance range of the derived value. The derived value may have a low or weak confidence rating if one or both of the accelerometer and LV pressure waveform data streams provide a heart rate value that is outside a predetermined tolerance range of the derived value.

Additionally, in some embodiments, the controller 202 is configured to determine an operating parameter of the blood pump assembly based on a multi-variable algorithm or function that takes into account one or more of the measured values and the determined cardiac characteristics or events. In some embodiments, for example, the controller 202 is configured to determine a target rotor speed based on a statistically weighted function with one or more of the following variables: heart rate, minimum ventricle pressure, ventricle pressure amplitude, and maximum dP/dt.

The signal-processing module 208 may output the determined value(s) to the pump control module 206 and/or the operator interface module 204. The operator interface module 204 may present the values to an operator using an input/output device 210 connected to the controller 202. The input/output device 210 may include, for example and without limitation, input devices including a keyboard, mouse, touchscreen, joystick(s), throttle(s), buttons, switches, and/or other input devices. For example, and without limitation, the input/output device 210 may include output devices including a display (e.g., a liquid crystal display (LCD), or an organic light emitting diode (OLED) display), speakers, indicator lights, instruments, and/or other output devices. In some embodiments, the operator interface module 204 is configured to receive at least one operator input such as a patient's clinical condition and provide the operator input to the pump control module 206 for use in controlling operation of the blood pump assembly 100. The patient's clinical condition may be clinical measurement or observation by a medical professional such as a heart characteristic or a medical diagnosis.

The pump control module 206 may use the determined value(s) to control operation of the blood pump assembly 100. Accordingly, the controller 202 may provide at least partially autonomous or closed-loop control of the blood pump assembly 100 by using the information received from the sensors to modify operation of the blood pump assembly 100. In some embodiments, the controller 202 provides operational control using any of the following based on the determined value(s): rotational speed of the rotor 114, mean VAD flow control, VAD flow amplitude control, minimum left ventricle LV control, left ventricle LV pressure amplitude control, and combinations thereof. For example, in some embodiments, the pump control module 206 is included on the on-board controller 116 and is configured to control a rotational speed of the rotor 114 based on the determined value(s) received from the signal-processing module 208. For example, the on-board controller 116 is operatively connected to the stator 112, and configured to control operation of the blood pump 102 by controlling the supply of electrical current to the stator 112 and thereby control rotation of the rotor 114. The pump control module 206 can be configured to control the rotor 114 in continuous flow operation and/or pulsatile flow operation.

In some embodiments, for example, the controller 202 is configured to control operation of the blood pump 102 to achieve a desired or preset cardiac characteristic. The controller 202 can periodically or continuously query the sensors 118, and compare the detected or determined values with one or more set points (e.g., a pressure set point, a flow set point). If the detected or determined values are different from the set point, the controller 202 can adjust the operation of the blood pump assembly 100 to achieve the set point. In some embodiments, the controller 202 is configured to determine if the difference between the characteristic and the set point exceeds a threshold difference before adjusting the operation of the blood pump assembly 100.

The set point can be established by operator input, for example, from a patient or a clinician, and can be stored in a memory device of the controller 202. The set point can be a fixed (i.e., time invariable) set point, or the set point can be a time variable set point. For example, a pressure set point can vary according to different phases of the cardiac cycle. That is, the pressure set point can be defined by a pressure profile that defines a desired or target pressure set point at different times or phases of the cardiac cycle. In addition, the operator input can include a plurality of set points and the controller 202 can select a set point based on a determined operating parameter and/or cardiac characteristic. In some embodiments, the set point(s) can include a nominal flow set point, a nominal rotor speed set point, a flow amplitude set point, and/or a set point for any other suitable operating parameter.

Further, in some embodiments, the set point may be adjusted in real time based on measurements received from the sensors 118 and/or the determined cardiac events or characteristics. For example, in some embodiments, the controller 202 is configured to increase or decrease a pressure set point based on the maximum slope of the measured ventricle pressure waveform (dP/dt). The maximum dP/dt is related to the contractility of the left ventricle, and can be used to adjust the pressure set point, and the resulting rotor speed, to achieve a desired left ventricle unloading. For example, the controller 202 may be configured to increase the pressure set point and/or the rotor speed based on the determined maximum dP/dt to increase left ventricle unloading. Further, in some embodiments, the controller 202 is configured to increase or decrease the pressure set point based on a determined heart rate of a patient. For example, an increased heart rate is indicative of increased need for cardiac output (e.g., from exercise), and the controller 202 can be configured to increase the pressure set point by a corresponding amount. Additionally or alternatively, the controller 202 may be configured to increase or decrease the pressure set point based on feedback received from the accelerometer 184 included in the blood pump assembly 100. For example, the controller 202 may determine that a user of the blood pump assembly 100 is exercising or engaged in rigorous activity based on feedback from the accelerometer 184, and increase the pressure set point or speed of the rotor accordingly.

In various embodiments, the controller 202 may determine certain pump operating and/or patient conditions based on measurements received from the sensors 118, and control the blood pump 102 accordingly. For example, Table 1 below is an exemplary correlation table illustrating how measured and/or determined parameters from sensors 118 may be associated and/or correlated with pump operating conditions and patient conditions. In particular, for a specific parameter, listed in the left-most column, Table 1 illustrates how a positive (+) or negative (−) deviation from an average or expected value for the parameter is correlated with a particular pump condition ("Suction") and/or one of several patient conditions ("Arrhythmia", "Hypertension", "Exercise", "Sleep", and "Recovery").

TABLE 1

| Parameter | Suction | Arrhythmia | Hypertension | Exercise | Sleep | Recovery |
|---|---|---|---|---|---|---|
| Rotor Displacement Amplitude | | | + | + | − | + |
| Rotor Displacement Amplitude Variability | + | + | | | | |
| Bearing Current Amplitude | | | + | + | − | + |
| Bearing Current Amplitude Variability | + | + | | | | |
| Minimum Flow | − | | − | | − | − |
| Minimum Flow Variability | + | + | | | | |
| Mean Flow | − | | − | + | − | − |
| Mean Flow Variability | | + | | | | |
| Maximum Flow | − | | | | | − |
| Maximum Flow | + | + | | | | |

TABLE 1-continued

| Parameter | Suction | Arrhythmia | Hypertension | Exercise | Sleep | Recovery |
|---|---|---|---|---|---|---|
| Variability |  |  |  |  |  |  |
| Flow Amplitude | − | − | + | + | − | + |
| Flow Amplitude Variability |  | + |  |  |  |  |
| Min dQ/dt | − | − | + | + | − | + |
| Min dQ/dt | − | − | + | + | − | + |
| Minimum LV Pressure | − |  | + | + | − | − |
| Minimum LV Pressure Variability |  | + |  |  |  |  |
| Mean LV Pressure | − |  | + | + | − | − |
| Mean LV Pressure Variability |  | + |  |  |  |  |
| Maximum LV Pressure | − |  | + | + | − |  |
| Maximum LV Pressure Variability |  | + |  |  |  |  |
| LV Pressure Amplitude |  | − | + |  | − | + |
| LV Pressure Amplitude Variability |  | + |  |  |  |  |
| Min dP/dt | − | − | + | + | − | + |
| Min dP/dt | − | − | + | + | − | + |
| Maximum LV Wall Velocity |  | − | + | + | − | + |
| Maximum LV Wall Velocity Variability |  | + |  |  |  |  |
| Pump Pitch Angle |  |  |  |  |  |  |
| Pump Roll Angle |  |  |  |  |  |  |
| Patient Activity Level |  |  |  | + | − |  |
| Minimum Aortic Pressure | − | − | + | + | − |  |
| Minimum Aortic Pressure Variability |  | + |  |  |  |  |
| Mean Aortic Pressure | − | − | + | + | − |  |
| Mean Aortic Pressure Variability |  | + |  |  |  |  |
| Maximum Aortic Pressure | − | − | + | + | − |  |
| Maximum Aortic Pressure Variability |  | + |  |  |  |  |
| Aortic Pressure Amplitude |  | − | + | + | − | + |
| Aortic Pressure Amplitude Variability |  | + |  |  |  |  |
| Min dP/dt | − | − | + | + | − | + |
| Min dP/dt | − | − | + | + | − | + |
| Heart Rate |  |  |  | + | − | − |
| Heart Rate Variability |  | + |  |  |  |  |
| Systolic Percentage |  |  |  | + |  |  |
| LV Systolic Elastance (Contractility) |  |  |  | + | − | + |
| LV Diastolic Elastance |  |  |  |  |  | + |
| LV Relaxation Constant |  |  |  |  |  |  |
| LV Filling Status |  |  | + | + | − | − |
| Aortic Valve Flow |  |  | + | + | − | + |
| Total Cardiac Output | − | − | − | + | − | + |
| VAD Work Share | − | + | − | − | + | − |
| Systemic Vascular Resistance (SVR) |  |  | + | − |  |  |
| Aortic Compliance |  |  |  |  |  |  |
| Overall Exertion Status |  |  |  | + | − |  |
| Inflow Occlusion |  | + |  |  |  |  |
| Outflow Occlusion |  |  |  |  |  |  |

In Table 1, the rotor displacement amplitude refers to the average peak-to-peak radial rotor displacement amplitude for a period of time, provided in units of micrometers (μm). The rotor displacement amplitude may be determined based on the data stream from the rotor position sensor 186. The bearing current amplitude refers to the average peak-to-peak bearing current amplitude over the period of time, provided in units of milliamperes (mA). The bearing current amplitude may be determined based on the data stream from the current sensors 182. The minimum, mean, and maximum flow values refer to the average minimum, mean, and maximum flow, respectively, for the period of time, provided in units of liters per minute. The flow amplitude refers to the average peak-to-peak flow amplitude rate for the period of time, provided in units of liters per minute. The flow values may be determined based on the data stream from the current sensors 180. The minimum, mean, and maximum LV pressure values refer to the average minimum, mean, and maximum left ventricular pressure values, respectively, for the period of time, provided in units of millimeters of mercury (mmHg). The LV pressure amplitude refers to the average peak-to-peak left ventricular pressure amplitude over the period of time, provided in units of mmHg. The LV pressure values may be determined based on the data stream from the inflow pressure sensors 178. The maximum LV wall velocity refers to the average peak left ventricular wall velocity during systole over the period of time, provided in units of millimeters per second. The maximum LV wall velocity may be determined based on the data stream from the accelerometer 184. The patient activity level refers to the overall patient activity level provided as a percentage of a maximum level indicated as an "exercise" state of the patient. The patient activity level may be determined based on the data stream from the accelerometer 184. The minimum, mean, and maximum aortic pressure refer to the average minimum, mean, and maximum aortic pressure, respectively, for the time period, provided in mmHg. The minimum, mean, and maximum aortic pressure may be determined based on the data stream from the current sensors 180 and the pressure sensors 178. The aortic pressure amplitude refers to the average peak-to-peak aortic pressure amplitude for the period of time, provided in mmHg. The aortic pressure amplitude may be determined based on the data stream from the current sensors 180 and the pressure sensors 178. The heart rate refers to the average heart rate for the period of time, provided in beats per minute. The heart rate variability refers to the variability in average heart rate over the period of time, provided as a percentage. The systolic percentage refers to the average percentage of a cardiac cycle spent in systole. The heart rate, heart rate variability, and systolic percentage may be determined based on the data streams from the rotor position sensor 186, the current sensors 182, the pressure sensors 178, and the accelerometer 184. The LV systolic elastance (contractility) refers to the slope of the LV elastance curve during systole (from a pressure-volume (PV) loop) which measures the contractility of the left ventricle, provided in units of mmHg/mL. The LV diastolic elastance refers to the slope of the left ventricular elastance curve during diastole (PV loop) which measures the diastolic stiffness of the left ventricle, provided in units of mmHg/mL. The LV filling status is a derived value that combines the minimum left ventricular pressure and flow amplitudes, and is provided as a percentage. The aortic valve flow refers to the estimated total flow through the aortic valve, provided in units of liters per minute. The total cardiac output refers to the estimated total cardiac output, provided in units of liters per minute.

The VAD work share refers to a percentage value of the total hydraulic work (systemic circulation) performed by the ventricular assist device compared to the left ventricle. The systemic vascular resistance refers to the average systemic resistance over the time period, provide in units of mmHg/liters per minute. The overall exertion status is a derived value that combines patient activity level, the LV filling status, and the heart rate, and is provided as a percentage. The inflow occlusion is a percentage of occlusion or blockage of the inflow (where 100% represents complete occlusion of the inflow and 0% represents completely open inflow). The outflow occlusion is a percentage of occlusion of the outflow.

A number of the parameters in Table 1 are derived from two or more measured or determined data streams. For example, the hemodynamic status parameters (the LV systolic elastance, the LV diastolic elastance, the LV filing status, the aortic valve flow, the total cardiac output, and the VAD work share) may be determined based on the left ventricle pressure waveform and the flow waveform. Also, the systemic vascular resistance, the overall exertion status, the inflow occlusion, and the outflow occlusion may be determined based on the left ventricle pressure waveform and the flow waveform.

As shown in Table 1, the parameters may be used to indicate pump operating conditions and patient conditions. For example, the controller 202 may recognize positive and negative variations (+/−) from an average or expected value for each parameter, and associate the variation with one or more conditions in Table 1, listed along the top row. The conditions indicated with a "+" are associated with a positive variation from average or expected value for the respective parameter. The conditions indicated with a "−" are associated with a negative variation from the average or expected value for the respective parameter.

In some embodiments, significance values may be assigned to the parameters when multiple parameters are associated with a single condition. The parameters may be weighted based on the significance values to provide a more accurate indication of the conditions. The significance values may be based on the quality ratings of the data feeds from sensors, the determined reliability of the parameter, and/or any other suitable factor. In such embodiments, the controller 202 may weight the parameters based on the significance values to determine a pump operating condition or patient condition indicated by the positive and negative deviations. For example, Table 2 below illustrates a list of exemplary significance ratings for the parameters listed in Table 1, using a scale in which 5 represents the greatest significance and 1 represents the lowest significance.

TABLE 2

| Parameter | Significance Rating (1-5) |
| --- | --- |
| Rotor Displacement Amplitude | 3 |
| Rotor Displacement Amplitude Variability | 2 |
| Bearing Current Amplitude | 3 |
| Bearing Current Amplitude Variability | 2 |
| Minimum Flow | 5 |
| Minimum Flow Variability | 3 |
| Mean Flow | 5 |
| Mean Flow Variability | 3 |
| Maximum Flow | 5 |
| Maximum Flow Variability | 3 |
| Flow Amplitude | 5 |
| Flow Amplitude Variability | 3 |
| Min dQ/dt | 2 |

TABLE 2-continued

| Parameter | Significance Rating (1-5) |
| --- | --- |
| Min dQ/dt | 2 |
| Minimum LV Pressure | 5 |
| Minimum LV Pressure Variability | 3 |
| Mean LV Pressure | 3 |
| Mean LV Pressure Variability | 1 |
| Maximum LV Pressure | 4 |
| Maximum LV Pressure Variability | 2 |
| LV Pressure Amplitude | 3 |
| LV Pressure Amplitude Variability | 2 |
| Min dP/dt | 3 |
| Min dP/dt | 3 |
| Maximum LV Wall Velocity | 4 |
| Maximum LV Wall Velocity Variability | 2 |
| Pump Pitch Angle | 3 |
| Pump Roll Angle | 3 |
| Patient Activity Level | 5 |
| Minimum Aortic Pressure | 4 |
| Minimum Aortic Pressure Variability | 2 |
| Mean Aortic Pressure | 5 |
| Mean Aortic Pressure Variability | 2 |
| Maximum Aortic Pressure | 4 |
| Maximum Aortic Pressure Variability | 2 |
| Aortic Pressure Amplitude | 4 |
| Aortic Pressure Amplitude Variability | 2 |
| Min dP/dt | 2 |
| Min dP/dt | 2 |
| Heart Rate | 5 |
| Heart Rate Variability | 4 |
| Systolic Percentage | 3 |
| LV Systolic Elastance (Contractility) | 5 |
| LV Diastolic Elastance | 3 |
| LV Relaxation Constant | 2 |
| LV Filling Status | 5 |
| Aortic Valve Flow | 5 |
| Total Cardiac Output | 5 |
| VAD Work Share | 5 |
| Systemic Vascular Resistance (SVR) | 3 |
| Aortic Compliance | 2 |
| Overall Exertion Status | 4 |
| Inflow Occlusion | 4 |
| Outflow Occlusion | 4 |

As noted above, the controller 202 may control the blood pump 102 based on the pump operating condition and/or patient condition determined from the data feeds received from the plurality of sensors 118. For example, Table 3 below illustrates an exemplary control scheme that may be implemented by controller 202 to control the blood pump 102. Specifically, Table 3 indicates under which conditions controller 202 will increase pump speed ("+") relative to a rotor speed set point, and under which conditions the controller 202 will decrease pump speed ("−") relative to a rotor speed set point.

TABLE 3

| | Suction | Arrhythmia | Hypertension | Exercise | Sleep | Recovery |
| --- | --- | --- | --- | --- | --- | --- |
| Change in Pump Speed | − | NA | + | + | − | − |

Additionally, in some embodiments, the controller 202 is configured to control the speed of the rotor 114 according to a speed profile that defines a time-variable speed set point of the rotor 114. In such embodiments, the controller 202 can be configured to modulate the speed of the rotor 114 to different speed set points within a single cardiac cycle of a patient's heart. This type of rotor speed control, also known as "synchronized pulsing", may be implemented by the controller 202 in any suitable manner that enables the blood pump assembly 100 to function as described herein. In some embodiments, for example, the controller 202 can be configured to increase the speed of the rotor 114 during systole (known as "co-pulsation"), or decrease the speed of the rotor 114 during systole (known as "counter-pulsation"). In yet other embodiments, the controller 202 can be configured to increase the speed of the rotor 114 over a first period of time during systole, and decrease the speed of the rotor 114 over a second period of time during systole. Additionally, synchronized pulsing of the rotor may be implemented by the controller 202 at varying intervals. For example, the controller 202 can be configured to modulate the speed of the rotor 114 to different speed set points within a single cardiac cycle of a patient's heart, or across more than one cardiac cycle of a patient's heart (for example, across two cardiac cycles).

In other embodiments, the controller 202 is configured to control the speed of the rotor 114 according to a fixed (i.e., time invariable) speed set point. In such embodiments, the controller 202 can be configured to control the speed of the rotor 114 to achieve an average speed equal to the speed set point. Rotor speed profiles and/or set points can be established by operator input, for example, from a patient or a clinician, and can be stored in a memory device of the controller 202.

Suitably, the control and sensing system 200 is configured to combine information from different sensors 118 to provide operating parameters for different operating states of the blood pump assembly 100. For example, the controller 202 may rely primarily on sensors 118 other than the current sensors 180, 182 when the blood pump assembly 100 is in a pulsing mode because the current sensors 180, 182 may not provide continuous data streams when the blood pump assembly 100 is operating in the pulsing mode.

In addition, the controller 202 may switch between the operating states based on the information received from the sensors 118. For example, the filtered data stream from the accelerometer 184 may indicate that the patient is active and the controller 202 may alter the pulse synchronization process based on the information from the accelerometer 184. In some embodiments, the controller 202 may select a pulse mode (e.g., co-pulse mode in which pump speed increases during systole, counter-pulse mode in which pump speed decreases during diastole, a combination of co-pulse and counter-pulse, or asynchronous pulse mode) of the blood pump assembly 100 based on the information from the plurality of sensors 118. In addition, the controller 202 may select one or more pulse parameters (e.g., amplitude, frequency, duration) based on the information from the plurality of sensors 118.

As noted above, one or more of the determined cardiac events or characteristics may be used by the controller 202 to perform closed-loop speed control of the pump rotor 114. For example, an increase in heart rate, minimum ventricle pressure, or ventricle pressure amplitude generally indicates an increased need for cardiac output. Accordingly, in some embodiments, the controller 202 is configured to adjust the speed of the rotor 114 by a corresponding amount when data from at least one of the sensors 118 indicates an increase in heart rate, minimum ventricle pressure, and/or ventricle pressure amplitude.

Additionally, in some embodiments, one or more of the determined cardiac events or characteristics can be used to examine and/or evaluate physiologic cardiac function. For example, the left ventricle pressure amplitude (i.e., the difference between maximum pressure and minimum pressure) is a combined indicator of both filling pressure and heart contractility. The minimum dP/dt can be used to evaluate the relaxation speed of the ventricle and to identify possible fibrosis or electrical conduction issues. The maximum dP/dt can be used to evaluate the systolic elastance curve of the ventricle, which is a direct measure of left ventricle functional performance. This may be used, for example, to detect left ventricle recovery, and to adjust the target pressure and/or rotor speed set points stored in controller 202 accordingly.

Figure 7:
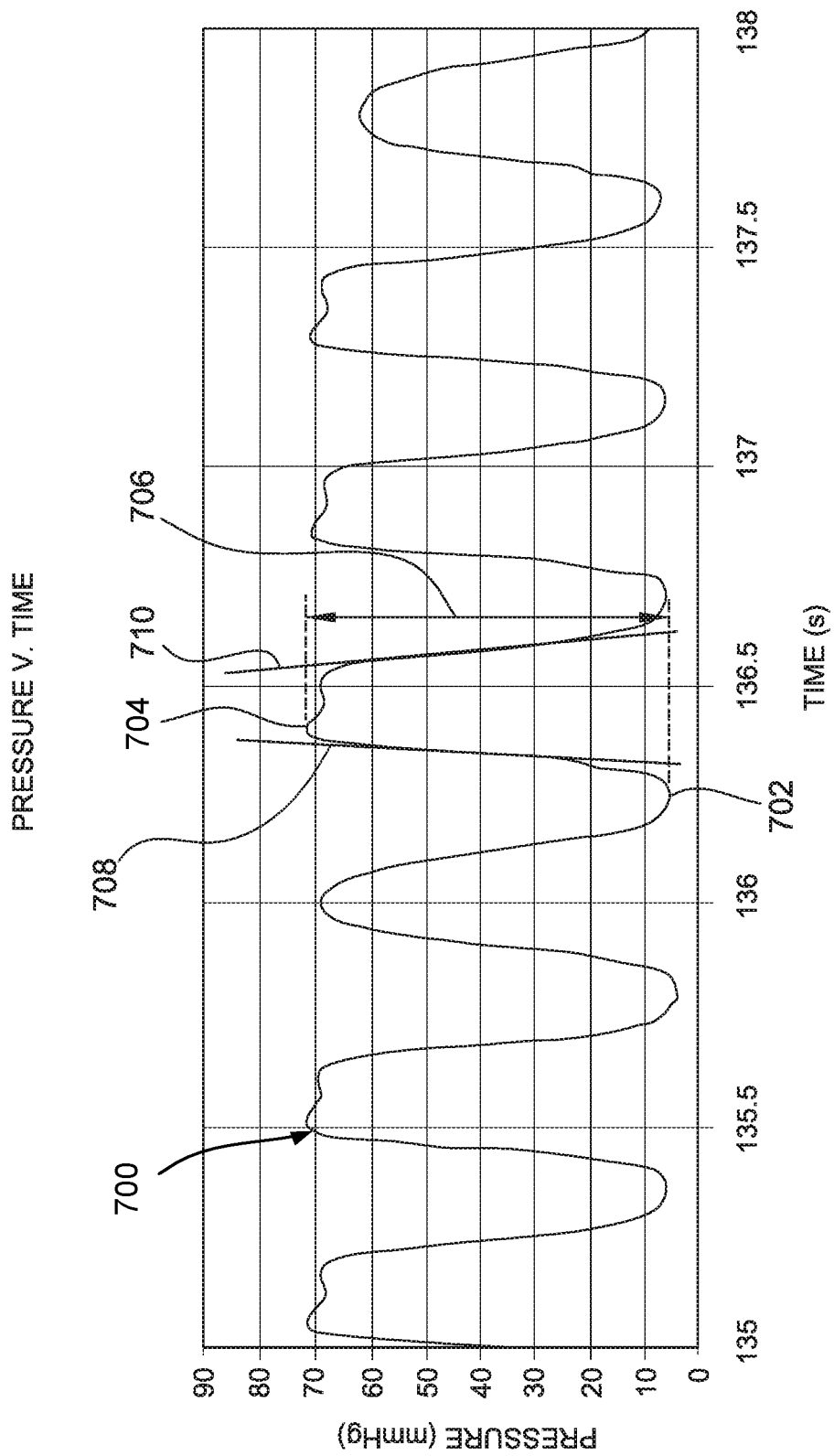
FIG. 7 is an example plot of data that may be collected and output by a pressure sensor included in the plurality of sensors shown in FIG. 6.

FIG. 7 is an example plot of data that may be collected and output by the pressure sensors 178 during operation of the blood pump assembly 100. The example plot illustrates the left ventricle pressure waveform 700 (i.e., pressure vs. time) over a period of about 3 seconds. The signal-processing module 208 may receive the waveform 700 and perform the filtering operation, e.g., the waveform extraction, and then determine one or more values based on the filtered data stream. For example, the controller 202 may be configured to determine the ventricular filling pressure or minimum pressure by identifying a local minimum pressure value on the pressure waveform within a single phase of the cardiac cycle. An example ventricular filling pressure value is identified at point 702 in FIG. 7. Additionally, the controller 202 may be configured to determine maximum systolic pressure by identifying a local maximum pressure value on the pressure waveform within a single phase of the cardiac cycle. An example maximum systolic pressure value is identified at point 704 in FIG. 7. The controller 202 may be further configured to determine the pressure amplitude 706 within a single cardiac phase of the pressure waveform by determining the difference between the maximum pressure 704 and the minimum pressure 702. The controller 202 may be further configured to determine contractility by determining the maximum slope 708 of the pressure waveform within the systolic phase of a single cardiac cycle. The controller 202 may also be configured to determine relaxation by determining the minimum slope 710 of the pressure waveform within the systolic phase of a single cardiac cycle. The controller 202 may also be configured to determine end-systolic pressure and end-diastolic pressure by identifying pressure values along the pressure waveform at the end of the systolic and diastolic phases, respectively, of the cardiac cycle. The controller 202 may also be configured to identify atrial kick pressure by identifying the pressure value at a localized maximum value on the pressure waveform within the diastolic phase of a single cardiac cycle (i.e., between the end of systole of a first cardiac cycle and the beginning of systole of a second cardiac cycle). The controller 202 may be configured to determine or identify the various phases of the cardiac cycle (e.g., systole and diastole) for the pressure waveform based on, for example, minimum pressure values, maximum pressure values, maximum slope values, and minimum slope values. For example, the controller 202 may be configured to determine that a certain portion of the pressure waveform corresponds to the systolic phase of the cardiac cycle by determining or identifying a region on the pressure waveform between the maximum slope and the minimum slope.

Figure 8:
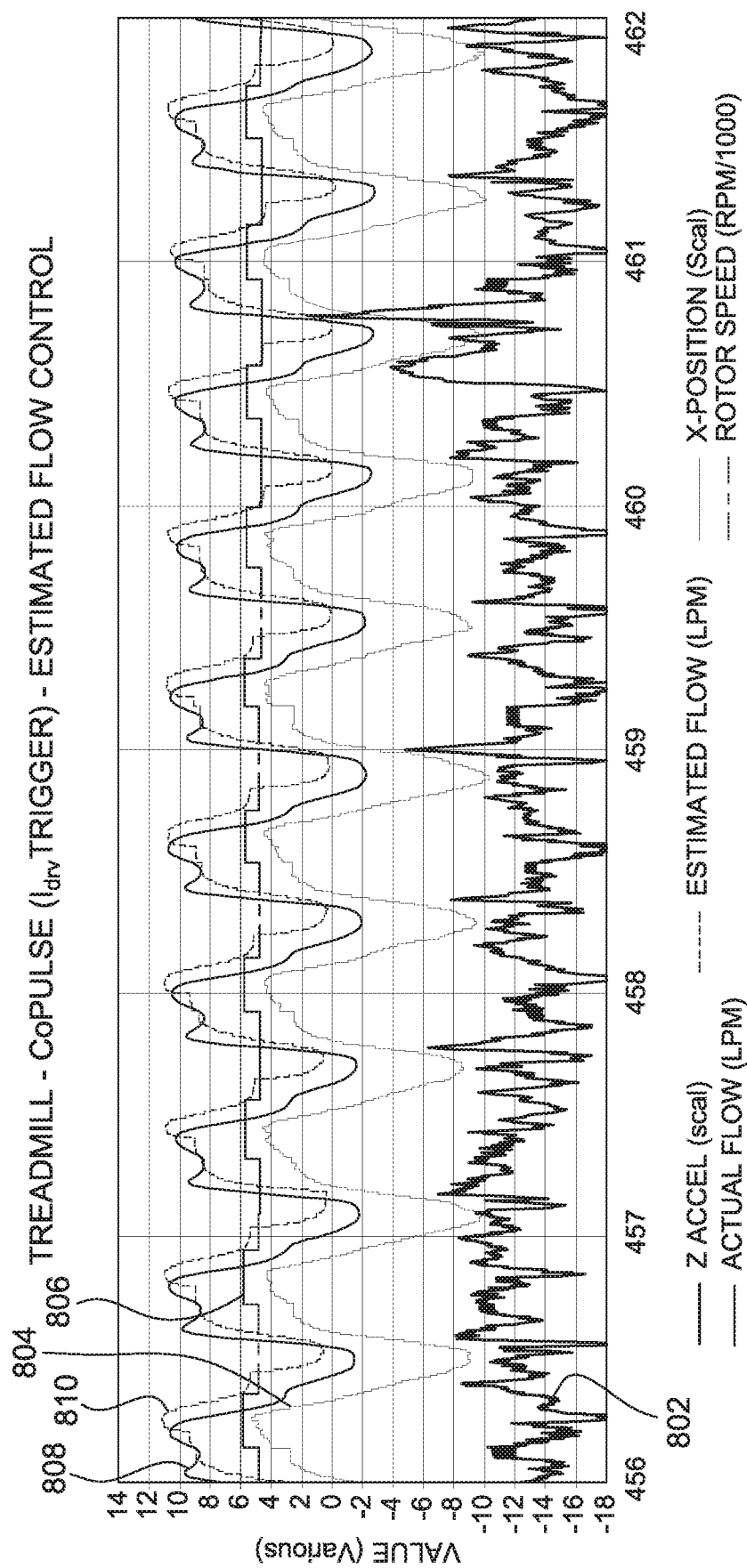
FIG. 8 is an example plot of data that may be collected and output by the plurality of sensors shown in FIG. 6.

FIG. 8 is an example plot of data that may be collected and output by the plurality of sensors. The example plot illustrates an acceleration waveform 802, a rotor position waveform 804, a rotor speed waveform 806, a flow waveform 808, and an estimated flow waveform 810. For example, the acceleration waveform 802 is based on data collected by the accelerometer 184. The rotor position waveform 804 is based on data collected by the rotor position sensor 186. The flow waveform 808 is based on values determined using data streams from one or more of the sensors 118, such as the first current sensor 180 and the pressure sensors 178. The data shown in the example plot was collected while the controller 202 was operating to synchronize the blood pump assembly 100 pulse to the heart pulse using measurements from the current sensors 180, 182. For example, the controller 202 identified when the instantaneous current/flow reading switched between a low and high value and changed operation of the blood pump assembly to accommodate changes. The instantaneous current/flow reading was considered a high value when the instantaneous current/flow reading was above an average flow value and considered a low value when instantaneous current/flow reading was below the average flow value. The controller 202 recognized the onset of systole when the instantaneous current/flow reading transitioned from a low value to a high value and indicated a change from diastolic flow to systolic flow. The controller 202 then operated the blood pump assembly 100 to account for the onset of systole.

Figure 9:
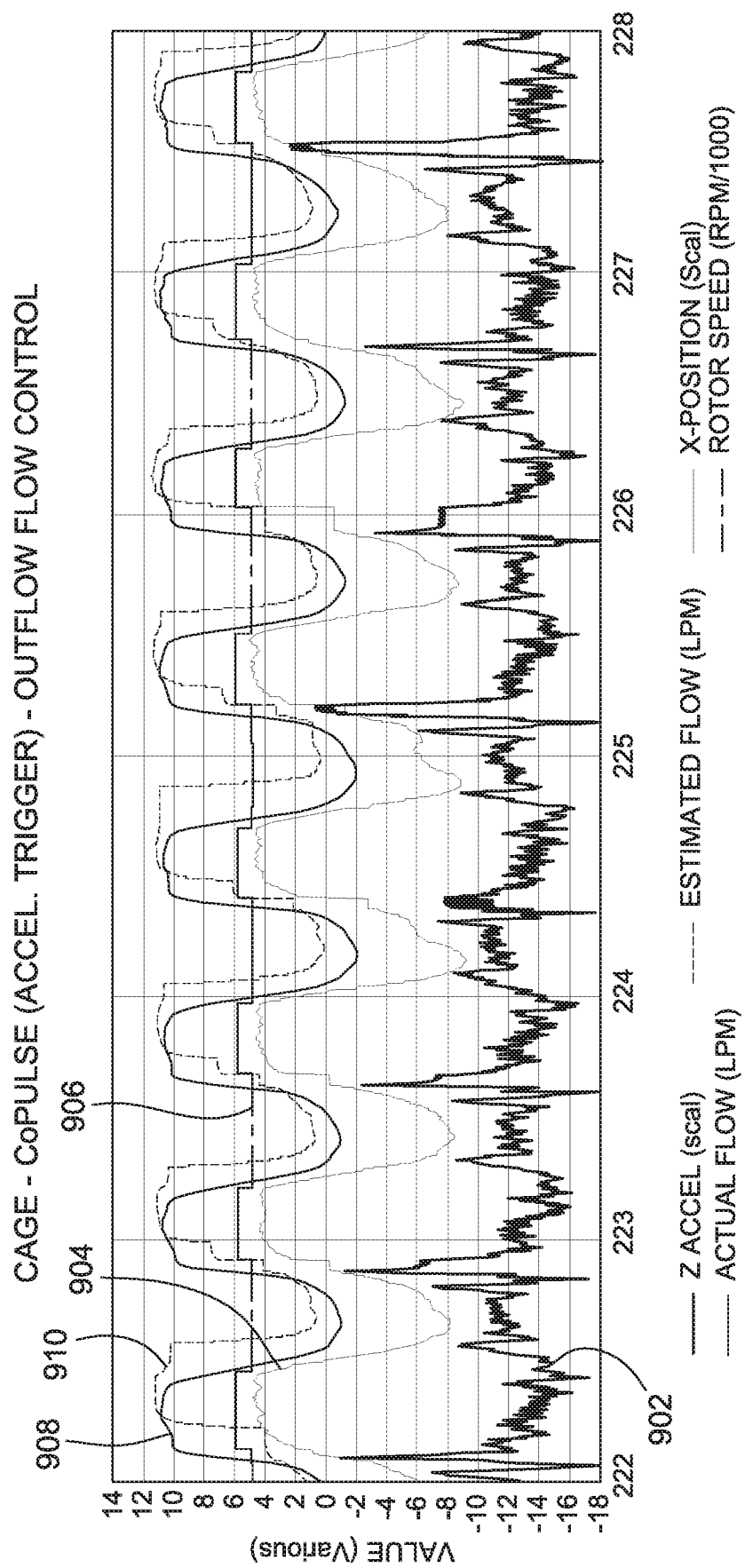
FIG. 9 is another example plot of data that may be collected and output by the plurality of sensors shown in FIG. 6.

FIG. 9 is another example plot of data that may be collected and output by the plurality of sensors. The example plot illustrates an acceleration waveform 902, a rotor position waveform 904, a rotor speed waveform 906, a flow waveform 908, and an estimated flow waveform 910. For example, the acceleration waveform 902 is based on data collected by the accelerometer 184. The rotor position waveform 904 is based on data collected by the rotor position sensor 186. The flow waveform 908 is based on values determined using data streams from one or more of the sensors 118. The data shown in the example plot was collected while the controller 202 was operating to synchronize the pulse of the blood pump assembly 100 to the heart pulse using measurements from an outflow flow sensor positioned on an exterior of the blood pump assembly 100.

Figure 10A:
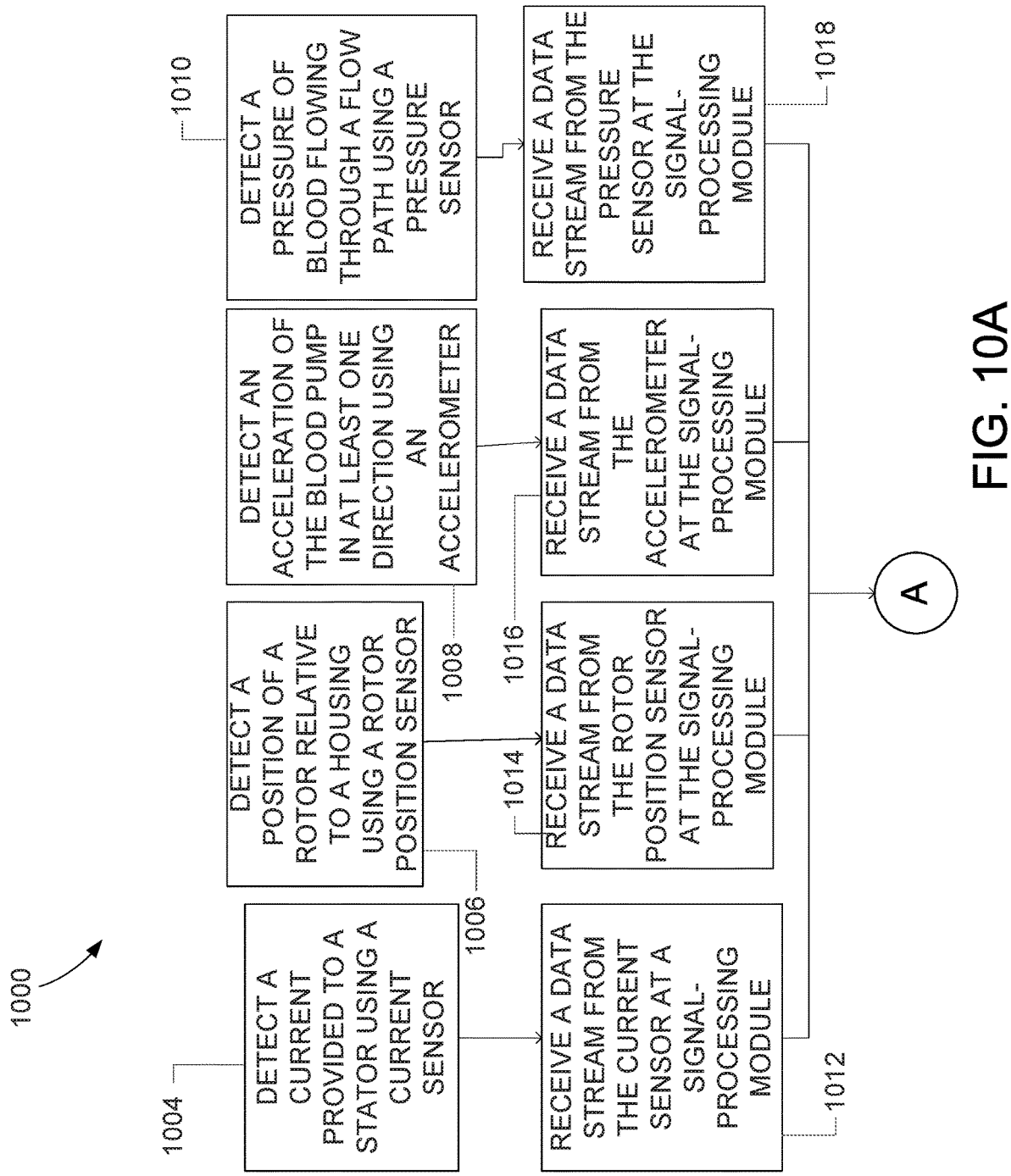
FIGS. 10A and 10B are flow diagrams illustrating one embodiment of a method of operating an implantable blood pump in a patient.
Figure 10B:
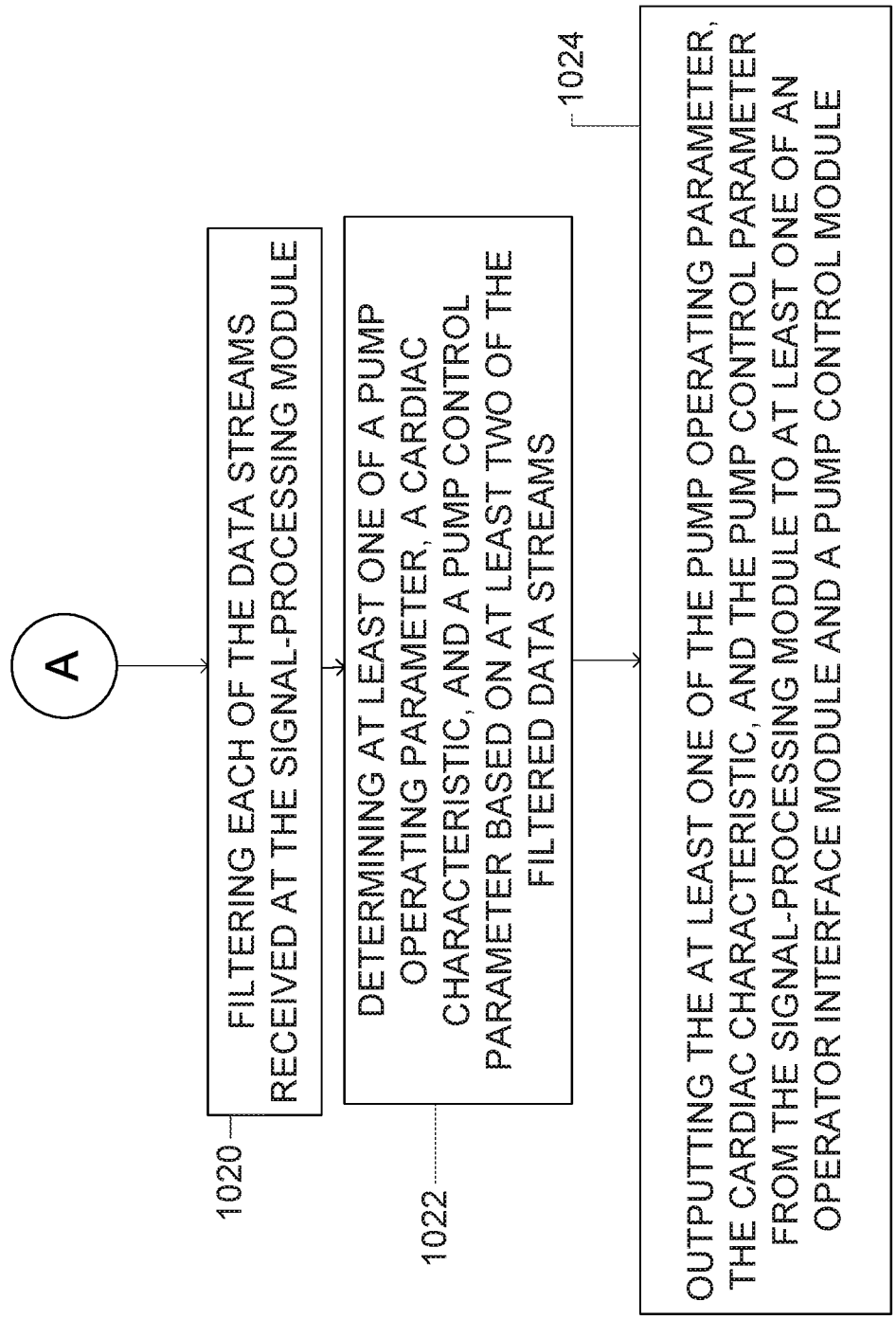

FIGS. 10A and 10B are flow diagrams illustrating one embodiment of a method 1000 of operating an implantable blood pump (e.g., blood pump 102) in a patient. In the illustrated embodiment, the method 1000 includes detecting 1004 a current provided to a stator (e.g., stator 112) using a current sensor (e.g., current sensors 180, 182), detecting 1006 a position of a rotor (e.g., rotor 114) relative to a housing (e.g., housing 104) using a rotor position sensor (e.g., rotor position sensor 186), detecting 1008 an acceleration of the blood pump in at least one direction using an accelerometer (e.g. accelerometer 184), and detecting 1010 a pressure of blood flowing through a flow path using a pressure sensor (e.g., pressure sensors 178). The method 1000 further includes receiving 1012 a data stream from the current sensor at a signal-processing module (e.g., signal-processing module 208) of a controller connected to the plurality of sensors, receiving 1014 a data stream from the rotor position sensor at the signal-processing module, receiving 1016 a data stream from the accelerometer at the signal-processing module, and receiving 1018 a data stream from the pressure sensor at the signal-processing module.

The method 1000 also includes filtering 1020, by a controller, each of the data streams received at the signal-processing module, and determining 1022, by the controller, at least one of a pump operating parameter, a cardiac characteristic, and a pump control parameter based on at least two of the filtered data streams. For example, in some embodiments, filtering the data streams includes performing a waveform feature extraction on the data streams. Features of the waveform (e.g., amplitude, frequency, wavelength) may indirectly correspond to pump operating conditions and/or to cardiac characteristic. Accordingly, one or more of the waveform features extracted from one or more of the data streams may be used by the controller to determine the pump operating parameter, the cardiac characteristic, or the pump control parameter.

The method 1000 further includes outputting 1024 the at least one of the pump operating parameter, the cardiac characteristic, and the pump control parameter from the signal-processing module to at least one of an operator interface module (e.g., operator interface module 204) and a pump control module (e.g., pump control module 206). The pump control module may control operation of the pump based on the value received from the signal-processing module. For example, in some embodiments, the pump control module controls a rotational speed of the rotor based on the value received from the signal-processing module. Also, in some embodiments, the operator interface module may provide the value received from the signal-processing module to an operator using a display.

In some embodiments, the method 1000 further includes generating a supplemental data stream based on at least two of the data streams received by the signal-processing module. For example, the signal-processing module may determine a waveform of a pressure of the blood flowing out of the blood pump through the outlet based on the current provided to the stator and the pressure of the blood flowing through the flow path. Accordingly, the supplemental data stream may represent a pressure of the patient's blood flow (e.g., an aortic pressure). The supplemental data stream may be filtered and combined with or compared to the other filtered data streams. Moreover, the controller may determine at least one of a pump operating parameter, a cardiac characteristic, and a pump control parameter based on the additional filtered data stream.

Also, in some embodiments, the method 1000 includes comparing the data streams received from each sensor. The data streams may be compared by determining a cardiac characteristic based on each data stream and comparing the determined cardiac characteristics. For example, the determined values may be evaluated to identify an outlier value, i.e., a determined value that differs significantly from at least two other values. In addition, the determined values may be compared to directly measured or estimated values to identify values that differ significantly from expected and/or measured cardiac characteristics. For example, in some embodiments, a patient's heart rate is determined based on each data stream. Each determined heart rate may be compared to an actual measured value of the patient's heart rate and/or a range of expected heart rates for the patient to check if the data streams are within preset accuracy ranges. In addition or alternatively, the determined heart rates are compared to each other to check if any of the data streams is significantly more/less accurate than other data streams.

In addition, in some embodiments, the method 1000 includes associating a quality rating with each data stream. For example, the signal-processing module may assign a numerical or other value to each data stream based on a point grading system or a predetermined scale (e.g., a scale of 1-5, with 1 being the lowest quality rating and 5 being the highest quality rating). The quality rating may allow the controller to weight the data streams and rely more heavily on data streams with higher quality ratings. In addition, in some embodiments, the controller may disregard data streams with quality ratings that do not meet a threshold value. Moreover, the controller may provide the quality rating of one or more of the data streams for presentation to the operator using an operator interface. In other embodiments, the data streams may be compared and rated in any suitable manner. For example, in some embodiments, the signal-processing module may compare and rate the data streams based on characteristics of the data streams such as signal strength.

Figure 11:
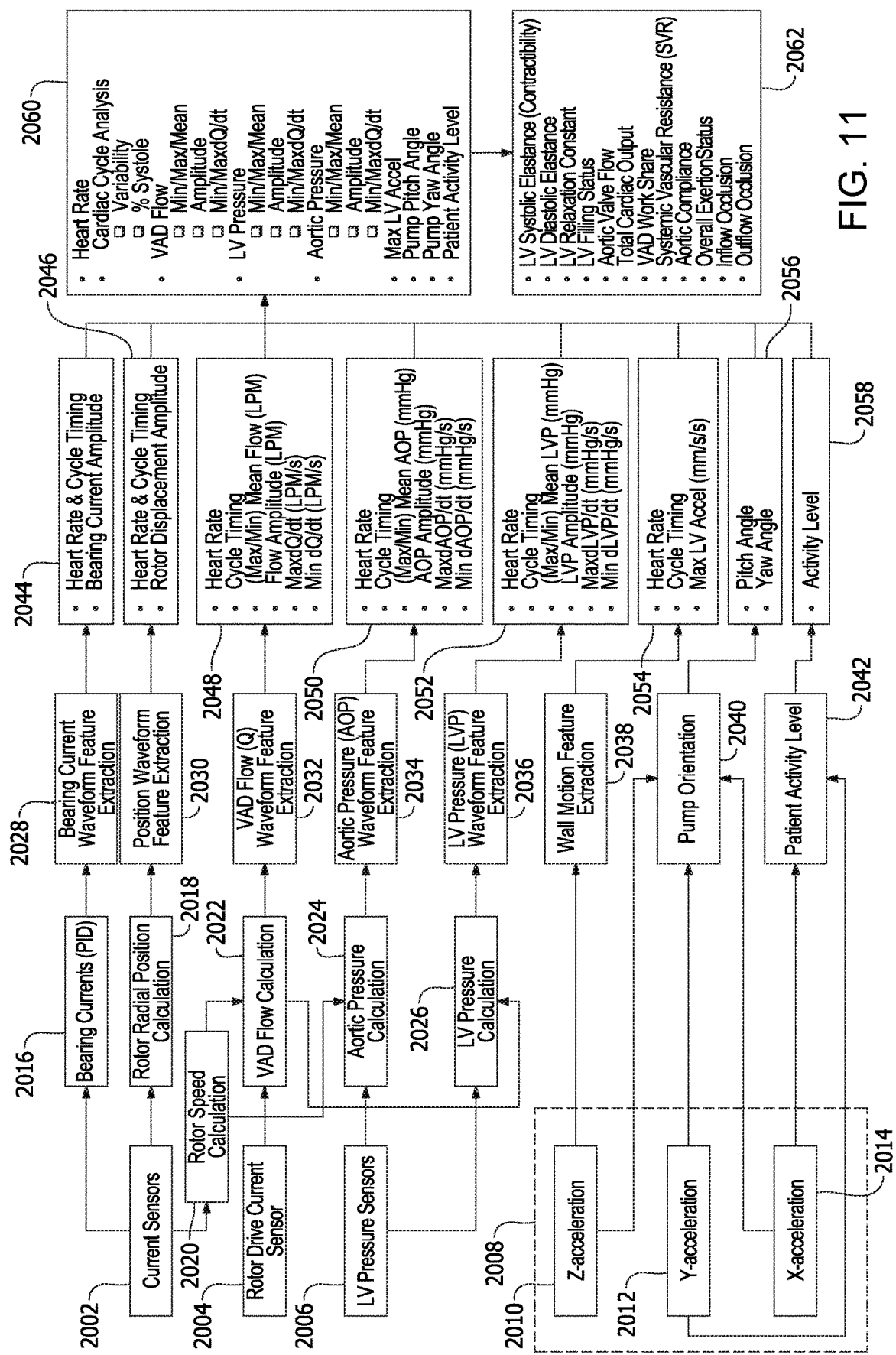
FIG. 11 is a flow diagram illustrating example data flow and processing of data collected by sensors during operation of an implantable blood pump in a patient.

FIG. 11 is a flow diagram illustrating example data flow and processing of data collected by sensors and processed by a controller (e.g., controller 202, shown in FIG. 6) during operation of an implantable blood pump (e.g., blood pump 102) in a patient. In the illustrated embodiment, data feeds are provided by current sensors 2002, a rotor drive current sensor 2004, a LV pressure sensor 2006, and an accelerometer 2008. The accelerometer 2008 includes a Z-acceleration component 2010, a Y-acceleration component 2012, and an X-acceleration component 2014.

The data feeds from the sensors 2002, 2004, 2006, 2008 are transformed and/or filtered to extract a plurality of parameters. For example, the data feeds from the current sensors 2002 undergo a bearing current transformation 2016 and a rotor radial position calculation 2018 to provide bearing current data and rotor radial position data, respectively. The resulting bearing current data and rotor radial position data undergo respective waveform feature extractions 2028 and 2030. The bearing current waveform feature extraction 2028 can be used to determine or extract various parameters 2044, including heart rate and cycle timing, and bearing current amplitude. Similarly, the rotor position waveform feature extraction 2030 can be used to determine various parameters 2046, including heart rate and cycle timing (e.g., as a redundant value), and bearing displacement amplitude.

Additionally, a rotor speed 2020 is calculated based on the data feed from the current sensors 2002 and/or rotor drive current sensor 2004. For example, the controller receives one or more data streams of the displacement and the angular position of the rotor and determines how much drive current and bearing current to provide for the rotor based on the data streams. The provided bearing currents and drive currents are measured by one or more of the current sensors 2002. The measured drive currents relate directly to rotor speed 2020. Accordingly, the calculated rotor speed 2020 can be determined based on the data feed from the rotor drive current sensor 2004. The calculated rotor speed 2020 is used to calculate 2022 a VAD flow value. The resulting VAD flow value undergoes a VAD flow waveform extraction 2032, which can be used to determine or extract various parameters 2048, including heart rate and cycle timing (e.g., as a redundant value), maximum, minimum, and mean flow (Q) (e.g., in liters per minute), flow amplitude (e.g., in liters per minute), and minimum and maximum slopes (dQ/dt) of the flow waveform.

Further, the calculated rotor speed 2020 is used in combination with the data feed from the LV pressure sensor 2006 to calculate 2024 an aortic pressure value. The resulting aortic pressure value undergoes an aortic pressure (AOP) waveform extraction 2034, which can be used to determine or extract various parameters 2050, including heart rate and cycle timing (e.g., as a redundant value), maximum, minimum, and mean aortic pressure values (e.g., in mmHg), aortic pressure amplitude (e.g., mmHg), and minimum and maximum slopes (dAOP/dt) of the aortic pressure waveform.

In addition, the calculated VAD flow value 2022 is used in combination with the data feed from the LV pressure sensor 2006 to calculate 2026 a left ventricular (LV) pressure value. The resulting LV pressure value undergoes an LV pressure (LVP) waveform extraction 2036, which can be used to determine or extract various parameters 2052, including heart rate and cycle timing (e.g., as a redundant value), maximum, minimum, and mean LV pressure values (e.g., in mmHg), LV pressure amplitude (e.g., mmHg), and minimum and maximum slopes (dLVP/dt) of the LV pressure waveform.

In the illustrated embodiment, the data feeds from the Z-acceleration component 2010, the Y-acceleration component 2012, and the X-acceleration component 2014 undergo feature extraction processes to determine additional parameters. For example, the data feed from the Z-acceleration component 2010 undergoes a wall motion feature extraction 2038 process to determine or extract various parameters 2054, including heart rate and cycle timing (e.g., as a redundant value), and maximum LV acceleration (e.g., in mm/s/s).

Additionally, in the illustrated embodiment, the data feeds from the Z-acceleration component 2010, the Y-acceleration component 2012, and the X-acceleration component 2012 are combined in a pump orientation determination function 2040 to determine an orientation of the blood pump 102. The pump orientation determination function 2040 can be used to determine or extract various parameters 2056, including a pitch angle of the blood pump 102 and a yaw angle of the blood pump 102.

Additionally, in the illustrated embodiment, the data feeds from the Y-acceleration component 2012 and the X-acceleration component 2012 are combined in a patient activity level determination function 2042 to determine a patient activity level 2058.

Also, two or more of the extracted parameters may be combined to provide combined parameters 2060 and/or signal quality metrics. The combined parameters 2060 can include, for example and without limitation: heart rate, cardiac cycle variability, cardiac cycle percentage systole, minimum flow through the blood pump assembly 100, maximum flow through the blood pump assembly 100, average flow through the blood pump assembly 100, amplitude of flow through the blood pump assembly 100, maximum rate of change of flow through the blood pump assembly 100, minimum rate of change of flow through the blood pump assembly 100, maximum aortic pressure, minimum aortic pressure, average aortic pressure, amplitude of aortic pressure, maximum rate of change of aortic pressure, minimum rate of change of aortic pressure, maximum left ventricle pressure, minimum left ventricle pressure, average left ventricle pressure, amplitude of left ventricle pressure, maximum rate of change of left ventricle pressure, minimum rate of change of left ventricle pressure, maximum left ventricle acceleration, pitch angle of blood pump assembly 100, yaw angle of the blood pump assembly 100, and activity level of the patient.

In addition, one or more patient clinical conditions 2062 may be determined based on the combined parameters 2060. The clinical conditions 2062 can include, for example and without limitation: LV systolic elastance (contractility), LV diastolic elastance, LV relaxation constant, LV filling status, aortic valve flow, total cardiac output, VAD work share, systemic vascular resistance, aortic compliance, overall exertion status of the patient, inflow occlusion, and outflow occlusion.

Although certain steps of the example methods are numbered, such numbering does not indicate that the steps must be performed in the order listed. Thus, particular steps need not be performed in the exact order they are presented, unless the description thereof specifically require such order. The steps may be performed in the order listed, or in another suitable order.

As described herein, the implantable blood pump assemblies of the present disclosure provide several advantages over previous VAD designs. For example, embodiments of the implantable blood pump assemblies disclosed herein include a plurality of sensors connected to a controller. By combining and/or comparing data streams from the plurality of sensors, the blood pump assemblies provide a greater scope of information and more reliable information than previous systems. Also, a controller is able to determine and provide information related to the signal accuracy of the plurality of sensors which can provide greater operator confidence in the accuracy and reliability of the system. Moreover, the controller may determine values that are statistically weighted based on the comparison of information from the plurality of sensors to ensure accurate information is used for operating the blood pump assemblies. In addition, the implantable blood pump assemblies may be operate at least partially autonomously using the information provided by the plurality of sensors and the closed-loop controls of the controller connected to the plurality of sensors.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A circulatory support system comprising:
    an implantable blood pump comprising:
        a housing defining an inlet, an outlet, a flow path extending from the inlet to the outlet, and an internal compartment separated from the flow path;
        a rotor positioned within the flow path and operable to pump blood from the inlet to the outlet;
        a stator positioned within the internal compartment and operable to drive the rotor;
        a plurality of sensors comprising at least two of the following:

a current sensor configured to detect a current provided to the stator;
a rotor position sensor configured to detect a position of the rotor relative to the housing;
an accelerometer configured to detect acceleration of the blood pump in at least one direction; and
a pressure sensor positioned between the inlet and the outlet and configured to detect a pressure of blood flowing through the flow path;
a controller connected to the plurality of sensors and including a signal-processing module and at least one of an operator interface module and a pump control module, wherein the signal-processing module is configured to:
receive, from each of the plurality of sensors, a data stream;
filter the data streams received from the plurality of sensors;
assign a statistical weight to each of the filtered data streams;
determine at least one of a pump operating parameter, a cardiac characteristic, and a pump control parameter based on at least two of the filtered data streams with the statistical weights applied to each of the filtered data streams; and
output a statistically weighted value for the at least one of the pump operating parameter, the cardiac characteristic, and the pump control parameter to at least one of the operator interface module and the pump control module.

2. The circulatory support system of claim 1, wherein the controller is configured to determine a signal quality parameter for each data stream received at the signal-processing module.

3. The circulatory support system of claim 1, wherein, for each data stream received from the plurality of sensors, the controller is configured to determine a cardiac characteristic based on the data stream, and compare the determined cardiac characteristics to each other.

4. The circulatory support system of claim 3, wherein the controller is configured to associate each data stream with a quality rating based on the comparison of the determined cardiac characteristics.

5. The circulatory support system of claim 1, wherein the controller includes the pump control module, and wherein the pump control module is configured to:
receive the at least one of the pump operating parameter, the cardiac characteristic, and the pump control parameter from the signal-processing module; and
control operation of the implantable blood pump based on the at least one of the pump operating parameter, the cardiac characteristic, and the pump control parameter.

6. The circulatory support system of claim 1, wherein the accelerometer is configured to detect acceleration of the pump in a first direction, a second direction, and a third direction, and wherein the controller is configured to determine a patient's activity level based on acceleration in at least one of the first direction, the second direction, and the third direction.

7. The circulatory support system of claim 1, wherein the controller is configured to generate a supplemental data stream based on data streams received from the current sensor and the pressure sensor, wherein the supplemental data stream includes a pressure of blood flowing out of the implantable blood pump through the outlet.

8. The circulatory support system of claim 1, wherein the controller includes the operator interface module, and wherein the operator interface module is configured to display the at least one of the pump operating parameter, the cardiac characteristic, and the pump control parameter.

9. The circulatory support system of claim 1, wherein the controller includes the operator interface module and the pump control module, wherein the operator interface is configured to receive at least one operator input relating to a patient's clinical condition and provide the operator input to the pump control module, and wherein the pump control module is configured to control operation of the pump based on the operator input and the at least one of the pump operating parameter, the cardiac characteristic, and the pump control parameter.

10. A method of operating an implantable blood pump, the blood pump including a housing defining an inlet, an outlet, a flow path extending from the inlet to the outlet, and an internal compartment separated from the flow path, a rotor positioned within the flow path and operable to pump blood from the inlet to the outlet, and a stator positioned within the internal compartment and operable to drive the rotor, the method comprising:
detecting, using a plurality of sensors, at least two of the following:
a current provided to the stator;
a position of the rotor relative to the housing;
an acceleration of the blood pump in at least one direction; and
a pressure of blood flowing through the flow path;
receiving, at a signal-processing module of a controller connected to the plurality of sensors, a data stream from each of the plurality of sensors;
filtering, by the controller, the data streams received from the plurality of sensors;
assigning a statistical weight to each of the filtered data streams;
determining, by the controller, at least one of a pump operating parameter, a cardiac characteristic, and a pump control parameter based on at least two of the filtered data streams with the statistical weights applied to each of the filtered data streams; and
outputting a statistically weighted value for the at least one of the pump operating parameter, the cardiac characteristic, and the pump control parameter from the signal-processing module to at least one of an operator interface module and a pump control module.

11. The method of claim 10 further comprising generating a supplemental data stream based on the current provided to the stator and the pressure of the blood flowing through the flow path, wherein the supplemental data stream includes a pressure of the blood flowing out of the blood pump through the outlet.

12. The method of claim 11, wherein determining at least one of a pump operating parameter, a cardiac characteristic, and a pump control parameter based on at least two of the filtered data streams comprises determining at least one of a pump operating parameter, a cardiac characteristic, and a pump control parameter based on at least two of the filtered data streams and the supplemental data stream.

13. The method of claim 10 further comprising determining a signal quality parameter for each data stream received at the signal-processing module.

14. The method of claim 10 further comprising determining, for each data stream received from the plurality of sensors, a cardiac characteristic based on the data stream, and comparing the determined cardiac characteristics.

15. The method of claim 14 further comprising associating each data stream with a quality rating based on the comparison of the determined cardiac characteristics.

16. The method of claim 10 further comprising adjusting a set point of the blood pump based on the at least one of the pump operating parameter, the cardiac characteristic, and the pump control parameter.

17. The method of claim 10, wherein determining at least one of a pump operating parameter, a cardiac characteristic, and a pump control parameter based on at least two of the filtered data streams comprises determining a heart rate of a patient.

18. The method of claim 10, wherein the data streams received from the plurality of sensors are waveform signals, and wherein filtering the data streams received from the plurality of sensors comprises performing a waveform feature extraction on the data streams.

19. An implantable blood pump comprising:
a housing defining an inlet, an outlet, a flow path extending from the inlet to the outlet, and an internal compartment separated from the flow path;
a rotor positioned within the flow path and operable to pump blood from the inlet to the outlet;
a stator positioned within the internal compartment and operable to drive the rotor;
a plurality of sensors comprising:
a current sensor configured to detect a current provided to the stator;
a rotor position sensor configured to detect a position of the rotor relative to the housing;
an accelerometer configured to detect acceleration of the blood pump in at least one direction; and
a pressure sensor positioned between the inlet and the outlet and configured to detect a pressure of blood flowing through the flow path,
wherein the plurality of sensors are connected to a controller configured to:
receive a data stream from each of the plurality of sensors;
filter the data streams received from the plurality of sensors;
assign a statistical weight to each of the filtered data streams; and
determine at least one of a pump operating parameter, a cardiac characteristic, and a pump control parameter based on the filtered data streams with the statistical weights applied to each of the filtered data streams.

20. The implantable blood pump of claim 19, wherein the plurality of sensors comprises a first current sensor connected to drive coils of the stator, and a second current sensor coupled to levitation coils of the stator.

21. The implantable blood pump of claim 19, wherein the accelerometer is configured to detect acceleration of the blood pump in a first direction parallel to a rotation axis of the rotor, a second direction perpendicular to the rotation axis, and a third direction perpendicular to the rotation axis and perpendicular to the second direction.

22. The implantable blood pump of claim 19, wherein the controller is configured to combine the filtered data streams based on an operating state of the implantable blood pump and according to a statistically weighted value system.

* * * * *